(12) United States Patent
Ogawa et al.

(10) Patent No.: US 8,288,729 B2
(45) Date of Patent: Oct. 16, 2012

(54) IMAGE PROCESSING APPARATUS, IMAGE PROCESSING METHOD, IMAGE PROCESSING PROGRAM, AND INFORMATION STORAGE MEDIUM HAVING IMAGE PROCESSING PROGRAM STORED THEREIN

(75) Inventors: Masaharu Ogawa, Kanagawa (JP); Nobuyuki Iwasaki, Kanagawa (JP); Takao Kuwabara, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 282 days.

(21) Appl. No.: 12/671,208

(22) PCT Filed: Jul. 15, 2008

(86) PCT No.: PCT/JP2008/062745
§ 371 (c)(1),
(2), (4) Date: Jun. 14, 2010

(87) PCT Pub. No.: WO2009/016959
PCT Pub. Date: Feb. 5, 2009

(65) Prior Publication Data
US 2010/0252743 A1    Oct. 7, 2010

(30) Foreign Application Priority Data
Jul. 30, 2007  (JP) ................................. 2007-197727

(51) Int. Cl.
*G01T 1/24*      (2006.01)
*H01L 25/00*    (2006.01)
*H01L 27/00*    (2006.01)
*H01L 27/146*  (2006.01)

(52) U.S. Cl. .................................. 250/370.08; 250/587
(58) Field of Classification Search ............. 250/370.08, 250/587
See application file for complete search history.

(56) References Cited

U.S. PATENT DOCUMENTS 5,648,660 A * 7/1997 Lee et al. ................. 250/370.09

FOREIGN PATENT DOCUMENTS

| JP | 10-260259 A | 9/1998 |
|---|---|---|
| JP | 2000-23953 A | 1/2000 |
| JP | 2003-319264 A | 11/2003 |
| JP | 2006-304213 A | 11/2006 |

* cited by examiner

*Primary Examiner* — Jessica Stultz
*Assistant Examiner* — Edwin Gunberg
(74) *Attorney, Agent, or Firm* — SOLARIS Intellectual Property Group, PLLC

(57) ABSTRACT

A first leakage current value output from each signal line is stored in a storage unit, with a charge corresponding to an emitted radiation being held in a radiographic image detector, when the radiation is uniformly emitted to the radiographic image detector. A second leakage current value is acquired which is output from each signal line, with a charge corresponding to the radiation dose being held in the radiographic image detector, when the radiation passing through an object is emitted to the radiographic image detector. When the first and second leakage current values are equal to each other for each line corresponding to each signal line, all pixels on the line are determined to belong to a background area (lines A and C).

18 Claims, 13 Drawing Sheets

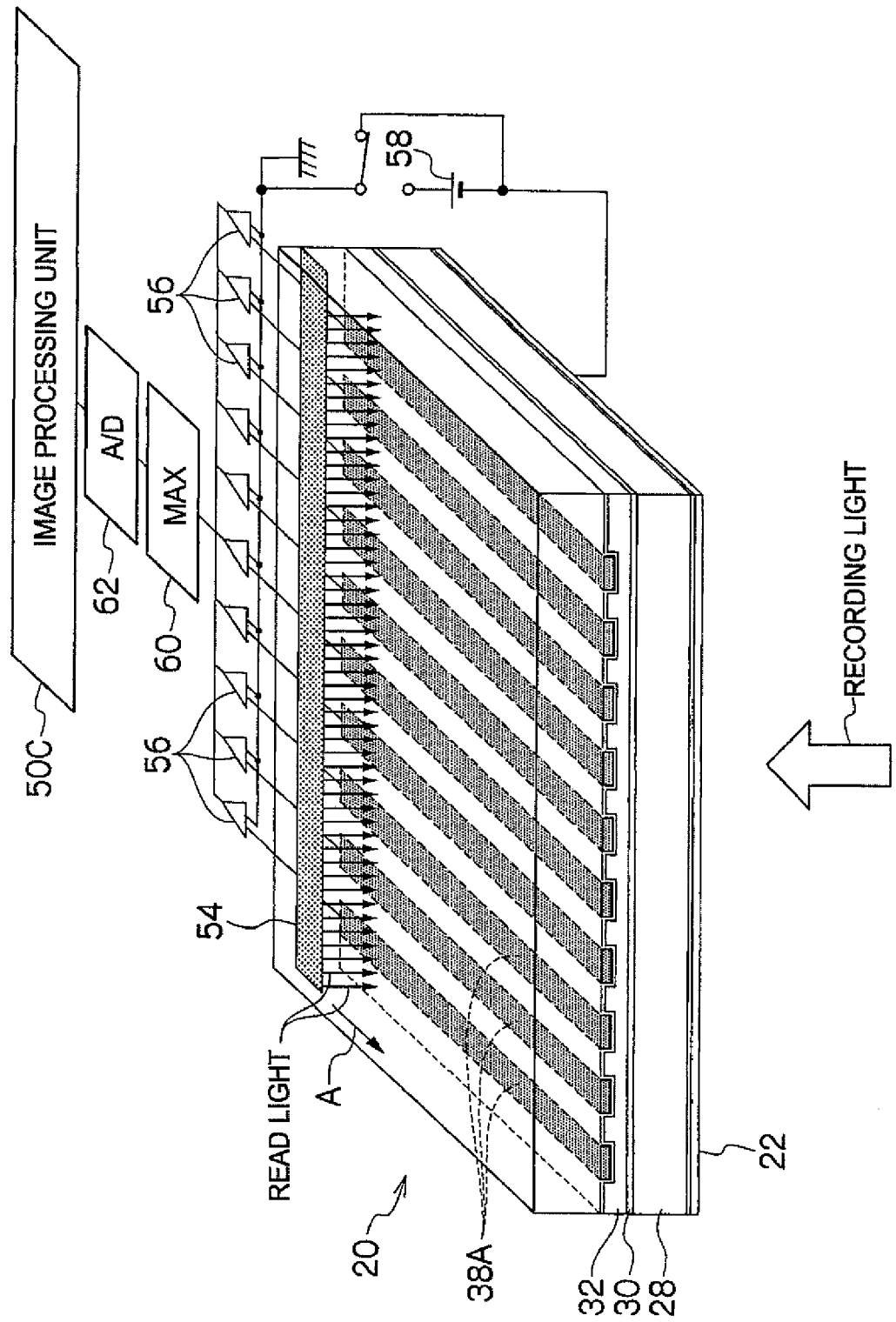

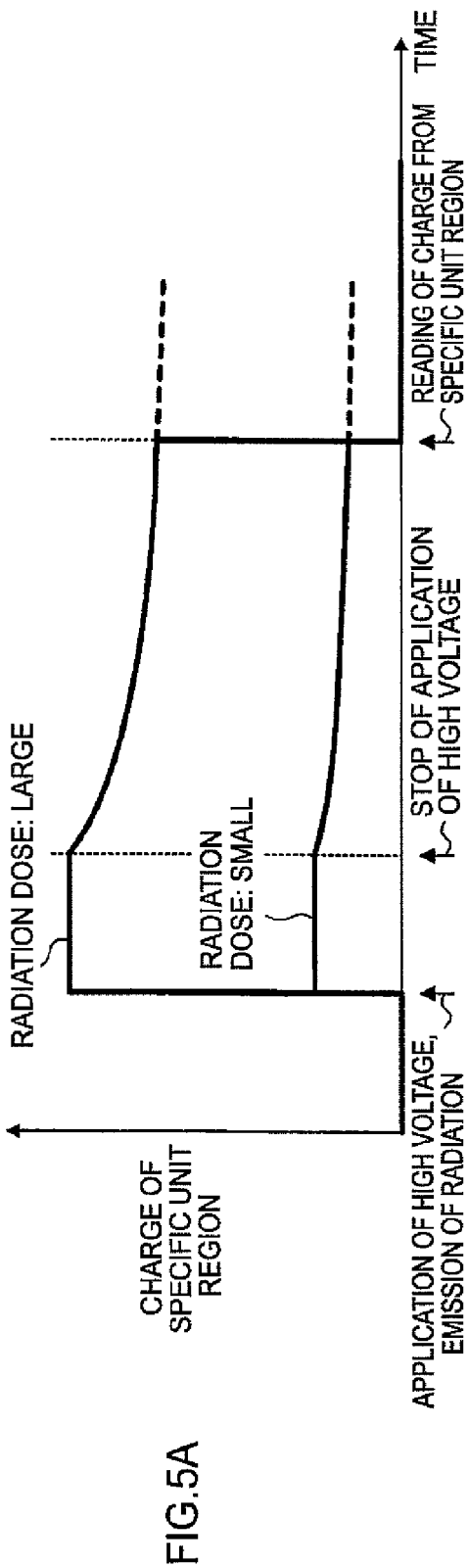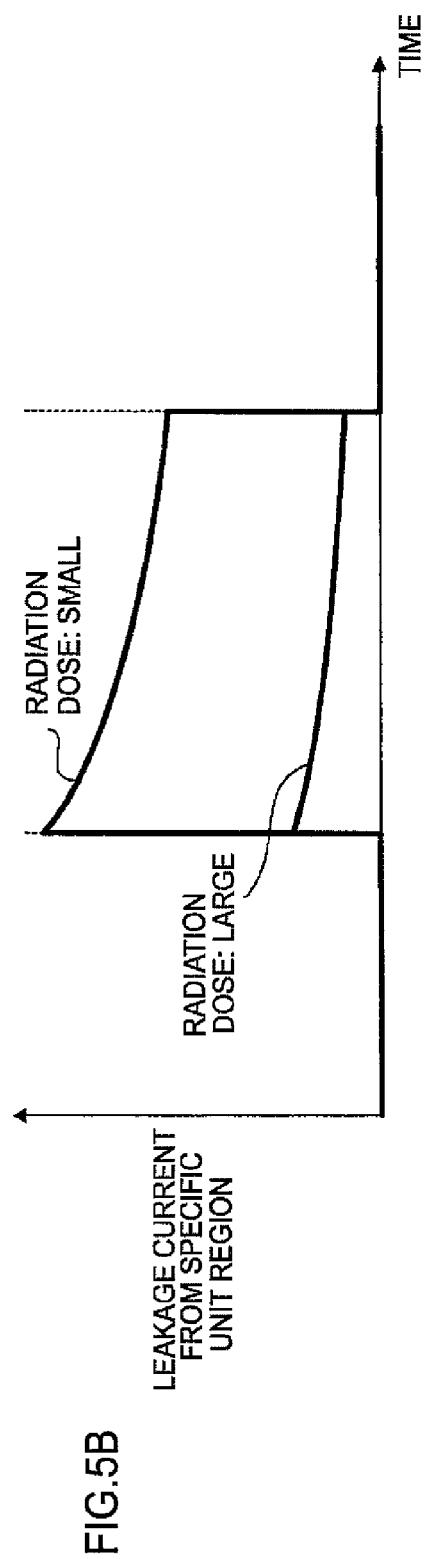

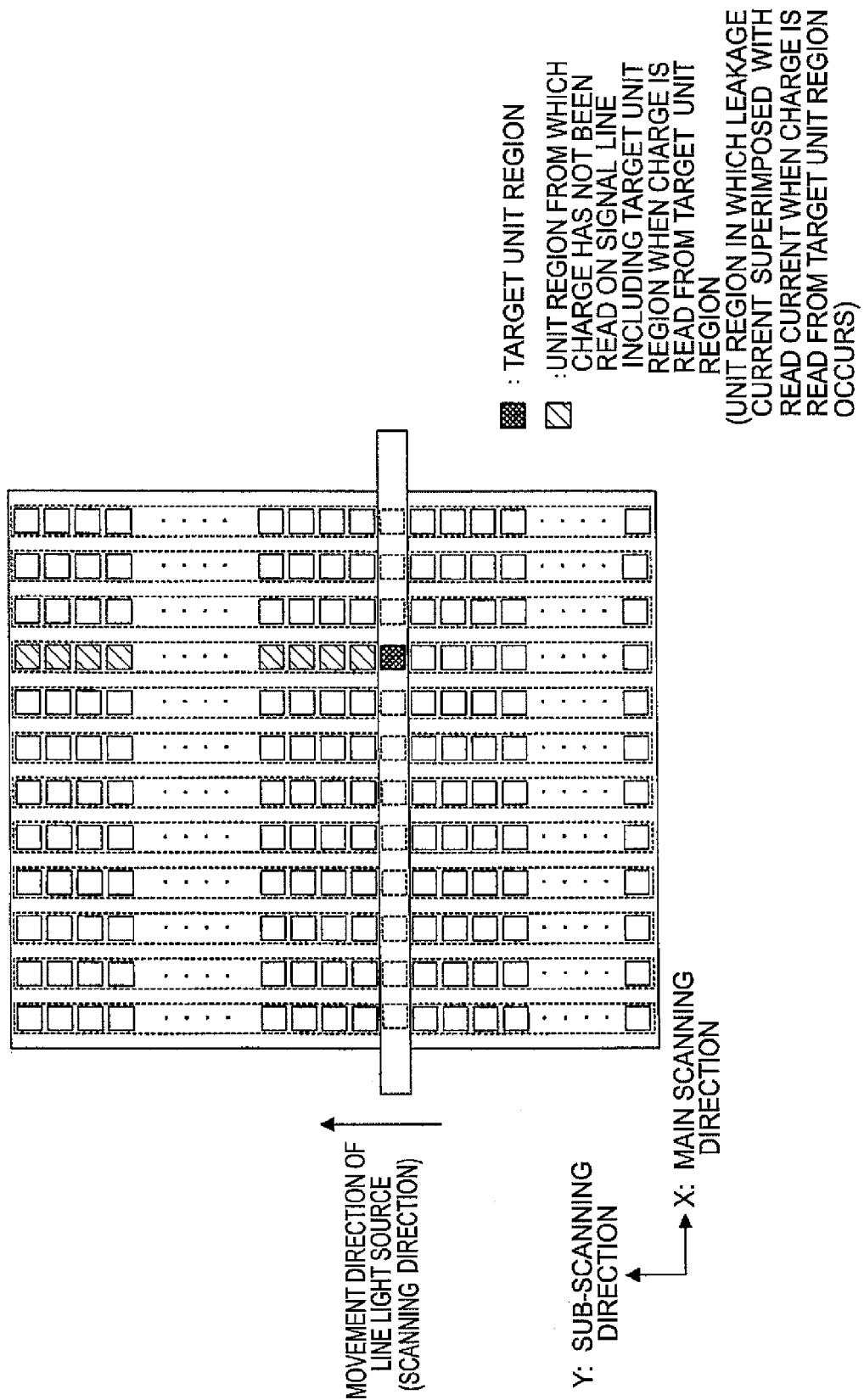

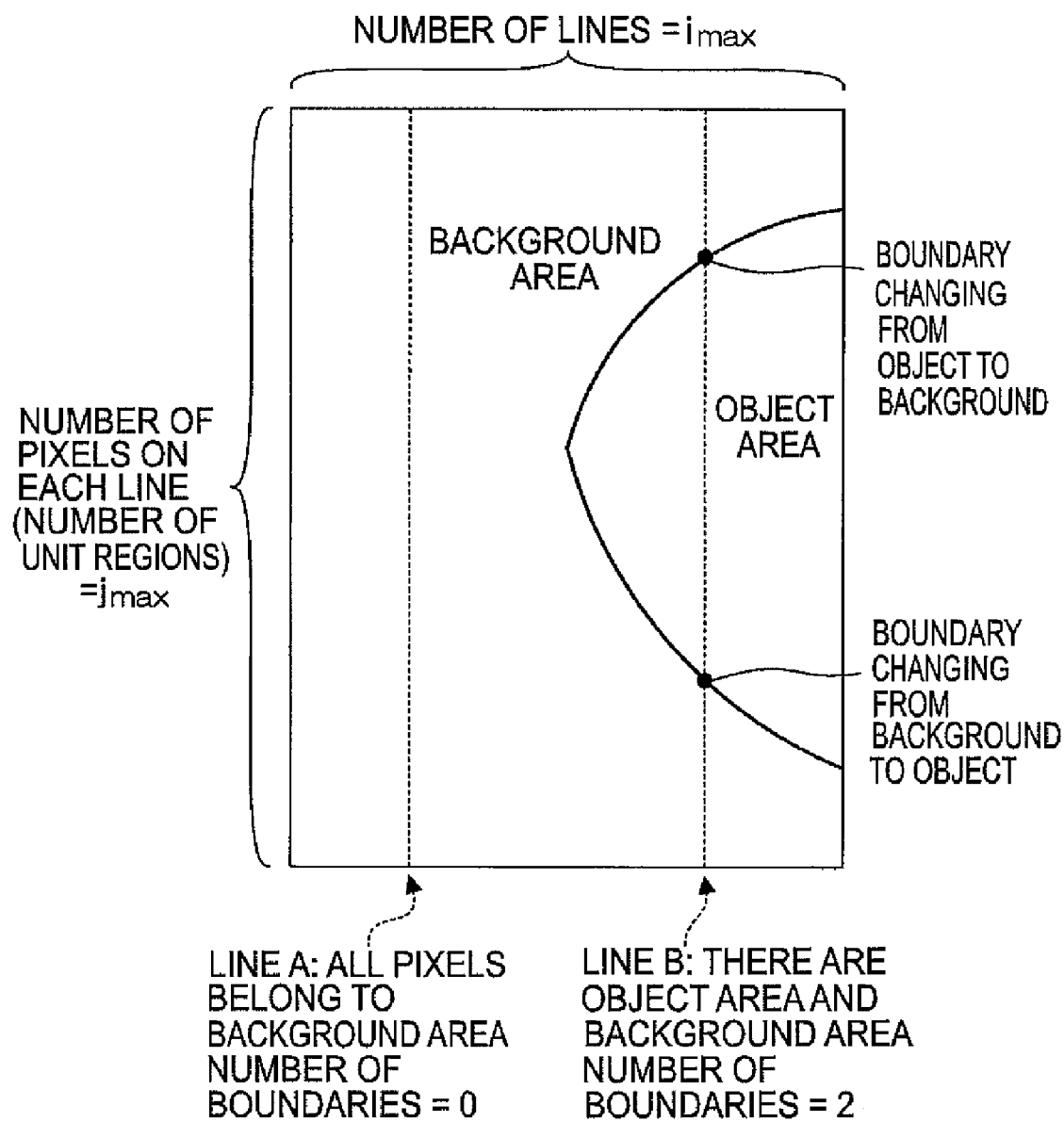

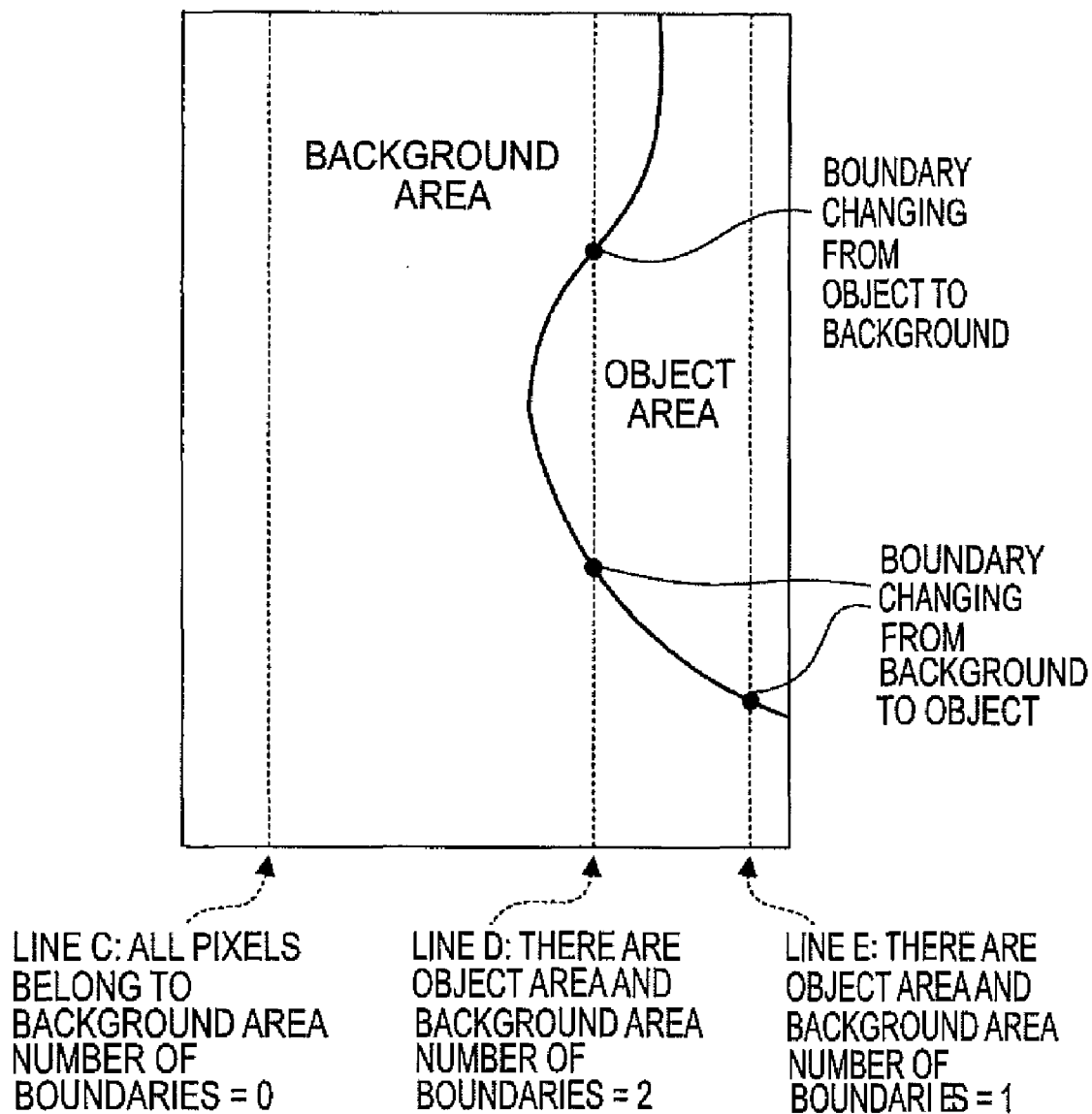

IMAGE PROCESSING APPARATUS, IMAGE PROCESSING METHOD, IMAGE PROCESSING PROGRAM, AND INFORMATION STORAGE MEDIUM HAVING IMAGE PROCESSING PROGRAM STORED THEREIN

TECHNICAL FIELD

The invention relates to an image processing apparatus, an image processing method, an image processing program, and an information storage medium, and more particularly, to an image processing apparatus that processes an image obtained by reading a charge from a radiographic image detector that converts an emitted radiation into charge and stores and holds the charge, an image processing method applicable to the image processing apparatus, an image processing program for allowing a computer to function as the image processing apparatus, and an information storage medium having the image processing program stored therein.

BACKGROUND ART

In radiography for medical diagnosis, systems have been proposed which obtain digital radiographic images. In the system, a radiation passing through an object is emitted to a radiographic image detector that is provided with a photoelectric conversion layer sensitive to radiation, a charge corresponding to the radiation dose emitted to the radiographic image detector is stored in the radiographic image detector, the change stored in the radiographic image detector is sequentially read as a read current from each unit region, and the read current is converted into digital data. In this type of radiographic image detector, when charge is read from a given unit region, a leakage current from the unit region from which charge has not been read yet superimposes the read current, which results in deterioration of the quality of the read image.

In order to solve this problem, Patent Document 1 discloses a technique for obtaining an image without the image being affected by a leakage current. In this technique, unit regions, each having a capacitor that stores charge converted in an X-ray conversion layer and a thin film transistor (TFT) that reads out the charge stored in the capacitor by on/off switching, are two-dimensionally arranged, and plural gate lines and plural signal lines are two-dimensionally arranged. In this structure, after charge is read out from all of the unit regions, the leakage current when charge is read from a specific unit region is calculated by adding the signal levels of all unit regions which are connected to the same data line as the specific unit region and from which charge has not been read during the reading of charge from the specific unit region and multiplying the added value by a coefficient A. The signal level of the specific unit region is corrected based on the calculated leakage current value. This process is performed on each unit region to obtain an image without the image being affected by the leakage current.

Patent document 1: Japan Patent Laid-Open No. 2006-304213

DISCLOSURE OF THE INVENTION

Problem to be Solved by the Invention

However, for example, in a technique for imaging the breast with radiation (also referred to as mammography), before a diagnosis image is displayed, a simple (for example, small) preview image is displayed. The operator determines whether an imaging range or a captured image is appropriate with reference to the preview image. When the operator determines that the imaging range or the captured image is not appropriate based on the displayed preview image, it is necessary to image again. Therefore, it is preferable to display the preview image as quickly as possible. In contrast, in the technique disclosed in Patent Document 1, after the image is read from the radiographic image detector, the leakage current is corrected. When the image after the leakage current is corrected is displayed as the preview image, it takes a long time to display the preview image. In order to solve this problem, it is considered that an image reading process and a leakage current correcting process are performed in parallel. However, when the leakage current correcting process is performed on (unit regions of) an area from which charge has already been read while there is an area from which charge has not been read yet (area whose value is not settled) in the image to be processed, the accuracy of correction is significantly reduced.

That is, the leakage current from each unit region which is disposed on the same signal line as a target unit region and from which charge has not been read during the reading of charge from the target unit region superimposes the read current when charge is read from an arbitrary target unit region of the radiation detector, and the amount of leakage current from each unit region depends on the amount of charge stored in each unit region. Therefore, in order to estimate the leakage current when charge is read from the target unit region, it is necessary to know the amount of charge stored in each unit region which is disposed on the same signal line as the target unit region and from which charge has not been read during the reading of charge from the target unit region. However, when there is a region from which charge has not been read in the image to be processed, the amount of charge stored in each unit region in the area is not known. Therefore, the accuracy of correction is significantly reduced.

The invention has been made in order to solve the above-mentioned problems, and an object of the invention is to provide an image processing apparatus, an image processing method, and an image processing program capable of estimating the distribution of object areas and background areas in an image that is stored and held as charge in a radiographic image detector when a radiation passing through an object is emitted to the radiographic image detector, before the image is completely read from the radiographic image detector.

Means for Solving Problem

In order to check the characteristics of the leakage current superimposed with the read current when the image is read from the radiographic image detector (when a charge corresponding to the radiation dose which is stored and held in the radiographic image detector is sequentially read as a current from each unit region), the inventors have conducted experiments with different radiation doses as follows: a predetermined radiation dose is uniformly emitted to a radiographic image detector (light-reading-type radiographic image detector) in which the charge stored in the unit region corresponding to a point to which the light is emitted as a current is output when light is emitted thereon, and the current flowing through signal lines which are provided in the radiographic image detector in a predetermined direction is measured without read light for reading an image (charge) being emitted.

In the experiments, since no read light is emitted to the light-reading-type radiographic image detector, the amount of current flowing through the signal lines should be zero.

However, actually, the flowing of a current through the signal line was observed in the experiment. The current can be represented by the sum of the amounts of leakage current from each unit region corresponding to the signal line on which current measurement has been performed, among all the unit regions of the radiographic image detector. The experiments proved that the amount of leakage current varied depending on the radiation dose; as the radiation dose was reduced, the amount of leakage current was also reduced; and the amount of leakage current when the radiation dose was about 100 mR was equal to the amount of read current when the radiation dose was about 0.1 mR, which was a very small value.

FIG. 1 is a histogram illustrating an image obtained by mammography, in which the horizontal axis indicates the radiation dose. As shown in FIG. 1, the image obtained by radiography is mainly divided into an object area and a background area. The radiation dose emitted to the object area (the radiation dose emitted to the radiographic image detector) is in the range of about 5 mR to 20 mR. The leakage current from the unit region belonging to the object area may be negligibly small. The radiation dose emitted to the background area is distributed in a range wider than that of the object area. The main distribution range is from 500 mR to 700 mR having 600 mR as the center. For example, as in the correction of the leakage current for generating a preview image, when leakage current correction requires a relatively low level of correction accuracy, it is supposed that the accuracy of correction is not significantly reduced even when an assumed value of the leakage current from each unit region belonging to the background area (for example, a value when it is assumed that the radiation dose is constant) is used.

These results show that it is possible to correct the influence of the leakage current without significantly reducing the accuracy of correction even when the image to be corrected is divided into the object area and the background area, the leakage current from the unit region belonging to the object area is neglected or corrected using an assumed value for the object area, and the leakage current from the unit region belonging to the background area is performed with simple leakage current correction based on an assumed value for the background area. When the distribution of the object area and the background area in the image to be corrected is known, the simple leakage current correction may be performed before the image is completely read. The distribution of the object area and the background area in the image may also be used for image processing other than the leakage current correction. For example, in the mammography, the object area is distributed in a certain range. Therefore, when the distribution of the object area and the background area is known before the image is completely read from the radiographic image detector, it is possible to perform image processing, such as a process of determining whether imaging fails based on the distribution (whether the object area is distributed in a predetermined range).

The inventors found that, when a radiation dose equal to or more than a predetermined value was uniformly emitted to the radiographic image detector, all the unit regions of the radiographic image detector became the background area (an amount of charge corresponding to the background area was stored and held in all the unit regions), the amount of leakage current from all the unit regions corresponded to the amount of leakage current from the unit regions belonging to the background area, and the amount of leakage current output through the signal lines provided in the radiographic image detector (a leakage current corresponding to the total sum of the amounts of leakage current from each unit region corresponding to the same signal line) also corresponded to the amount of leakage current from the unit regions belonging to the background area. On the other hand, when the radiation passing through the object was emitted to the radiographic image detector, some of the unit regions of the radiographic image detector became the object area (the amount of charge stored and held was reduced to a value corresponding to the object area in some unit regions), the leakage current from some unit regions was negligibly small, and the leakage current output through the signal lines provided in the radiographic image detector (a leakage current corresponding to the total sum of the amounts of leakage current from each unit region corresponding to the same signal line) was also reduced accordingly; and when the radiation passing through the object was emitted to the radiographic image detector, the amount of decrease (rate of decrease) in the leakage current output through the signal line substantially corresponded to the number (ratio) of unit regions belonging to the object area among the unit regions corresponding to the signal line.

According to a first aspect of the invention, an image processing apparatus includes: a storage unit that stores a first leakage current value which is output through a signal line provided in a predetermined direction in a radiographic image detector which converts emitted radiation into a charge and stores and holds the charge, a charge corresponding to uniformly emitted radiation being held in the radiographic image detector; and an estimating unit that estimates a ratio between an object area and a background area on a line arranged along the signal line in an image which is held as the charge in the radiographic image detector, or estimates lengths of the object area and the background area, based on the ratio between the first leakage current value stored in the storage unit, and a second leakage current value output through the signal line when radiation passing through an object is emitted to the radiographic image detector, a charge corresponding to the radiation passing through the object being held in the radiographic image detector.

In the image forming apparatus according to the first aspect of the invention, the storage unit stores the first leakage current value output through the signal lines which are provided in the radiographic image detector, which converts an emitted radiation into a charge and stores and holds the charge, in a predetermined direction, with a charge corresponding to a uniformly emitted radiation being held in the radiographic image detector. The radiation dose uniformly emitted to the radiographic image detector in order to obtain the first leakage current value may be adjusted such that the amount of charge corresponding to the background area is stored and held in each unit region of the radiographic image detector. In addition, the radiographic image detector may preferably have, for example, a structure in which plural read electrodes arranged in a direction intersecting the predetermined direction are provided as the signal lines, and when light is emitted, the amount of charge held in the unit region corresponding to a point to which the light is emitted is output as a current through the corresponding read electrode (a so-called light-reading-type radiographic image detector). In this case, the charge stored in the radiographic image detector may be read by scanning the point of the radiographic image detector to which light is emitted in a predetermined direction. Instead of the radiographic image detector having the above-mentioned structure, a radiographic image detector having the following structure (a so-called TFT type) may be used: the charge generated by an emitted radiation is stored, and the stored charge is read from each unit region by turning on or off switching elements such as thin film transistors (TFT).

As described above, the leakage current value (second leakage current value) output through the signal line when the radiation passing through the object is emitted to the radiographic image detector is reduced with respect to the first leakage current value from the unit region on the same signal line according to the number (ratio or length) of unit regions belonging to the object area among the unit regions corresponding to the signal line. Therefore, in the image forming apparatus according to the first aspect of the invention, the estimating unit estimates the ratio between the object area and the background area on the line arranged along the signal line in an image which is held as the charge in the radiographic image detector, or the lengths of the object area and the background area, based on the ratio between the first leakage current value stored in the storage unit and a second leakage current value output through the signal line, with a charge corresponding to the radiation passing through the object being held in the radiographic image detector, when the radiation passing through an object is emitted to the radiographic image detector. Specifically, the estimating unit estimates the ratio between the object area and the background area as follows. For example, when the first leakage current value is I1 and the second leakage current value is I2, the ratio $R_B$ of the background area may be calculated by $R_B = I_2/I_1$ and the ratio $R_O$ of the object area may be calculated by $Ro=1-R_B$, or the ratios may be calculated by $R_O=(I_1-I_2)/I_i$ and $R_B=1-R_O$. The estimating unit estimates the lengths of the object area and the background area as follows: when the total length of the line along the signal line is L, the length $L_O$ of the object area may be calculated by $R_O \times L$, and the length $L_B$ of the background area may be calculated by $R_B \times L$.

In this way, it is possible to estimate the distribution of the object area and the background area in the image which is stored and held as charge in the radiographic image detector when the radiation passing through the object is emitted, before the reading of the image from the radiographic image detector is completed, specifically, before the image is read from the radiographic image detector. Therefore, before the reading of the image from the radiographic image detector is completed (before the image is read from the radiographic image detector), the estimation result of the distribution of the object area and the background area is obtained. Therefore, it is possible to perform a process using the estimation result (for example, leakage current correction) in parallel with a process of reading the charge stored and held in each unit region of the radiographic image detector (the reading of the image from the radiographic image detector). In addition, in the image forming apparatus according to the first aspect of the invention, when plural signal lines are provided in the radiographic image detector, the estimating unit may preferably estimate the ratio between the object area and the background area on each signal line or the lengths of the object area and the background area. In this way, it is possible to detect the substantially two-dimensional distribution of the object area and the background area in the image that is stored and held as charge in the radiographic image detector when the radiation passing through the object is emitted.

In the image forming apparatus according to the first aspect of the invention, the ratio between the object area and the background area on the line arranged along the signal line or the lengths of the object area and the background area, which are estimated as the distribution of the object area and the background area, can be used for, for example, leakage current correction, determination of whether there is an object area, or the substantial distribution thereof. However, the ratio or the lengths are not sufficient, as information, to perform image processing, such as a process of generating an image indicating the position of the boundary between the object area and the background area. Therefore, when the number of boundaries between the object area and the background area on the line arranged along the signal line or the upper limit thereof is known, the estimating unit may preferably estimate the ratio between the object area and the background area on the line arranged along the signal line or the lengths of the object area and the background area, and estimate the position of the boundary between the object area and the background area on the line arranged along the signal line based on the estimated ratio and the known number of boundaries.

In this way, it is possible to perform image processing using the estimation result of the position of the boundary between the object area and the background area (the estimation result of the position of the boundary between the object area and the background area may be used in leakage current correction) in parallel with a process of reading the charge stored and held in each unit region of the radiographic image detector (the reading of an image from the radiographic image detector). A typical example of the image in which the number of boundaries between the object area and the background area on the line arranged along the signal line or the upper limit thereof is known is an image having the breast as an object (specifically, a cranio-caudal (CC) view and a medio-lateral oblique (MLO) view). However, other images having parts of the human body other than the breast as objects may be used.

In the imaging processing apparatus in which, when the number of boundaries between the object area and the background area on the line arranged along the signal line or the upper limit thereof is known, the estimating unit estimates the ratio between the object area and the background area on the line arranged along the signal line or the lengths of the object area and the background area, and estimates the position of the boundary between the object area and the background area on the line arranged along the signal line based on the estimated ratio and the known number of boundaries, the estimating unit may estimate the position of the boundary between the object area and the background area as follows. That is, when the number of boundaries between the object area and the background area on the line arranged along the signal line is 1, the estimating unit may determine whether the unit region from which charge has been read through the signal line as quickly as possible belongs to the object area or the background area based on the amount of the charge (the amount of read current), and estimate the position of the boundary between the object area and the background area based on the determination result and the estimation result of the ratio between the object area and the background area or the lengths of the object area and the background area. Specifically, when it is determined that the unit region from which charge has been read as quickly as possible belongs to the object area, it is possible to determine that the object area is disposed on the upstream side in the direction in which charge is read. Therefore, it is estimated that the boundary between the object area and the background area is disposed at a position which is spaced $R_O \times L$ (where L indicates the total length of the line arranged along the signal line) from the upstream end in the direction in which charge is read. When it is determined that the unit region belongs to the background area, it is possible to determine that the background area is disposed on the upstream side in the direction in which charge is read. Therefore, it is estimated that the boundary between the object area and the background area is disposed at a position which is spaced $R_B \times L$ (where L indicates the total length of the line arranged along the signal line) from the upstream end in the direction in which charge is read.

When the number of boundaries between the object area and the background area on the line arranged along the signal line is two or more, the estimating unit may detect the position of the boundary between the object area and the background area in the range of the line arranged along the signal line for which charge has been read as a current, based on a variation in the current when the charge is sequentially read as the current from each unit region read through the signal line, and estimate the position of the boundary between the object area and the background area in the range of the line arranged along the signal line for which charge has not been read, based on the detected position of the boundary and the estimated ratio between the object area and the background area or the estimated lengths of the object area and the background area.

Specifically, when the length of the range of the line arranged along the signal line in which charge is read as a current (the range in which charge has already been read) is $L_F$, the ratio of the object area in the range in which charge has already been read is $R_{OF}$, and the ratio of the background area in the range is $R_{BF}$, the estimating unit determines whether the unit region in which a current variation occurs belongs to the object area or the background area based on the variation in the current. When it is determined that the unit region in which a current variation occurs belongs to the object area, it is possible to determine that there is the object area on the upstream side in the direction in which charge is read. Therefore, it is estimated that the boundary between the object area and the background area is disposed at a position which is spaced $R_O \times L - (R_{OF}/R_{BF}) \times L_F$ from the detected boundary position. When it is determined that the unit region in which a current variation occurs belongs to the object area, it is possible to determine that there is the object area on the upstream side in the direction in which charge is read. Therefore, it is estimated that the boundary between the object area and the background area is disposed at a position which is spaced $R_B \times L - (R_{BF}/R_{OF}) \times L_F$ from the detected boundary position.

In the above-mentioned structure, when the number of boundaries between the object area and the background area on the line arranged along the signal line is three or more, the estimating unit may perform a process of detecting the position of the boundary between the object area and the background area plural times, based on a variation in current, and estimate the position of the boundary between the object area and the background area in the range of the line arranged along the signal line for which charge has not been read when the remaining number of non-detected boundaries is 1.

In the imaging processing apparatus in which, when the number of boundaries between the object area and the background area on the line arranged along the signal line or the upper limit thereof is known, the estimating unit estimates the ratio between the object area and the background area on the line arranged along the signal line or the lengths of the object area and the background area, and estimates the position of the boundary between the object area and the background area on the line arranged along the signal line based on the estimated ratio and the known number of boundaries, as described above, when the number of boundaries between the object area and the background area on the line arranged along the signal line is two or more, the estimation of the position of the boundary between the object area and the background area on the line arranged along the signal line is performed when the remaining number of non-detected boundaries is 1. However, the invention is not limited thereto. For example, in an image having the breast as an object, since imaging is performed such that the object area is disposed at a predetermined position in the image (for example, in the image having the breast as an object, imaging is performed such that the object area is disposed at the center of the image), the estimating unit may estimate the position of the boundary between the object area and the background area on the line arranged along the signal line, based on a predetermined assumed value of the ratio between plural background areas on the line arranged along the signal line, and the estimated ratio between the object area and the background area or the estimated lengths of the object area and the background area.

For example, in the image in which the background areas are disposed at both ends of the line arranged along the signal line (the number of background areas on the line arranged along the signal line is 2, and the number of boundaries between the object area and the background area is 2) and the object area is disposed at the center of the image, the position of the boundary between the object area and the background area is estimated assuming that the assumed value of the ratio of two background areas on the line is set to "1:1" (50%) in advance and the background areas at both ends of the line have the same length. In this case, the accuracy of estimating the position of the boundary between the object area and the background area is reduced, but it is possible to estimate the boundary position even when the image is not read from the radiographic image detector since only the second leakage current value is known.

In the image forming apparatus according to the first aspect of the invention, when it is considered that the radiation dose emitted to the object varies if necessary, for example, the storage unit may store the first leakage current values when plural different radiation doses are uniformly emitted to the radiographic image detector, and the estimating unit may preferably perform the estimation based on the first leakage current value corresponding to the radiation dose emitted to the object of the first leakage current values stored in the storage unit. In this way, even when the radiation dose emitted to the object is changed, it is possible to accurately estimate the ratio between the object area and the background area or the lengths of the object area and the background area.

In the image forming apparatus according to the first aspect of the invention, when plural signal lines are provided in the radiographic image detector, it is considered that the first leakage current values of the signal lines are likely to be different from each other due to a variation in the characteristics of the unit regions corresponding to each signal line. In this case, for example, the storage unit may store the first leakage current value of each of the signal lines, and the estimating unit may preferably perform the estimation for each of the signal lines based on the corresponding first leakage current value among the first leakage current values stored for each signal line in the storage unit. In this way, it is possible to prevent the accuracy of estimating the ratio between the object area and the background area or the lengths thereof from being reduced due to a variation in the characteristics of the unit regions corresponding to each signal line.

The image processing apparatus according to the first aspect of the invention, or the imaging processing apparatus in which, when the number of boundaries between the object area and the background area on the line arranged along the signal line or the upper limit thereof is known, the estimating unit estimates the ratio between the object area and the background area on the line arranged along the signal line or the lengths of the object area and the background area, and estimates the position of the boundary between the object area and the background area on the line arranged along the signal line based on the estimated ratio and the known number of boundaries may preferably further include, for example, a leakage current correcting unit that performs a leakage current correcting process of estimating a leakage current superimposed with a read current when the charge is read from each of the unit regions belonging to at least the object area among the read unit regions corresponding to the signal line, based on the ratio between the object area and the background area on the line arranged along the signal line, the lengths of the object area and the background area, or the position of the boundary between the object area and the background area estimated by the estimating unit, and correcting corresponding data based on the estimation result of the leakage current. As described above, since the estimation result of the ratio between the object area and the background area on the line arranged along the signal line, the lengths of the object area and the background area, or the position of the boundary between the object area and the background area is used, it is possible to start leakage current correction before the image is completely read from the radiographic image detector at the latest and thus rapidly complete the leakage current correction. In addition, in the image forming apparatus having the above-mentioned structure, the leakage current correction may be performed on each unit region belonging to the background area.

In the image forming apparatus having the above-mentioned structure, the leakage current correcting unit may preferably calculate the number of unit regions belonging to the object area and the number of unit regions belonging to the background area, among the unit regions which are disposed on the same signal line as the unit region, which is a objection of correction, in the predetermined direction and from which the charge has not been read during the reading of charge from the unit region, which is the objection of the correction, based on the ratio between the object area and the background area on the line arranged along the signal line, the lengths of the object area and the background area, or the position of the boundary between the object area and the background area estimated by the estimating unit, exclude the unit regions belonging to the object area from a leakage current estimation object, and estimate only the leakage current from the unit regions belonging to the background area, thereby estimating the leakage current superimposed with the read current when the charge of the unit region, which is the objection of the correction, is read. In this way, it is possible to reduce the number of unit regions, which are leakage current estimation objects, and simplify leakage current correction. Therefore, it is possible to rapidly complete the leakage current correction.

The imaging processing apparatus in which, when the number of boundaries between the object area and the background area on the line arranged along the signal line or the upper limit thereof is known, the estimating unit estimates the ratio between the object area and the background area on the line arranged along the signal line or the lengths of the object area and the background area, and estimates the position of the boundary between the object area and the background area on the line arranged along the signal line based on the estimated ratio and the known number of boundaries may further include an image processing unit that performs image processing to generate a boundary indication image indicating the position of the boundary between the object area and the background area based on the position of the boundary between the object area and the background area on the line arranged along the signal line which is estimated by the estimating unit.

In the image forming apparatus having the above-mentioned structure, the leakage current correcting unit or the image processing unit may preferably perform the leakage current correction or the image processing in parallel with a process of sequentially reading the charge from each unit region read through the signal line as a current. In this way, it is possible to rapidly complete the leakage current correction by the leakage current correcting unit or the image processing by the image processing unit.

The image forming apparatus having the above-mentioned structure may further include a display control unit that controls a display unit to display an image obtained by the leakage current correction by the leakage current correcting unit or an image obtained by the image processing by the image processing unit. In this way, it is possible to rapidly complete the leakage current correction by the leakage current correcting unit or the image processing by the image processing unit. Therefore, the display unit can rapidly display an image under the control of the display control unit.

According to a second aspect of the invention, an image processing method includes: storing, in a storage unit, a first leakage current value which is output through a signal line provided in a predetermined direction in a radiographic image detector, which converts emitted radiation into a charge and stores and holds the charge, a charge corresponding to uniformly emitted radiation being held in the radiographic image detector; and estimating a ratio between an object area and a background area on a line arranged along the signal line in an image which is held as the charge in the radiographic image detector, or estimating the lengths of the object area and the background area, based on the ratio between the first leakage current value stored in the storage unit, and a second leakage current value output through the signal line when radiation passing through an object is emitted to the radiographic image detector, a charge corresponding to the radiation passing through the object being held in the radiographic image detector. According to the above-mentioned aspect, similar to the image processing apparatus according to the first aspect of the invention, it is possible to estimate the distribution of the object area and the background area in the image which is stored and held as charge in the radiographic image detector when the radiation passing through the object is emitted, before the reading of the image from the radiographic image detector is completed.

According to a third aspect of the invention, there is provided an image processing program for allowing a computer, connected to a storage unit that stores a first leakage current value which is output through a signal line provided in a predetermined direction in a radiographic image detector which converts emitted radiation into a charge and stores and holds the charge, a charge corresponding to uniformly emitted radiation being held in the radiographic image detector, to function as: an estimating unit that estimates a ratio between an object area and a background area on a line arranged along the signal line in an image which is held as the charge in the radiographic image detector, or estimates lengths of the object area and the background area, based on the ratio between the first leakage current value stored in the storage unit, and a second leakage current value output through the signal line when radiation passing through an object is emitted to the radiographic image detector, a charge corresponding to the radiation passing through the object being held in the radiographic image detector.

The image processing program according to the third aspect of the invention allows the computer connected to the storage unit to function as the estimating unit. Therefore, when the computer executes the image processing program according to the third aspect of the invention, the computer functions as image processing apparatus according to the first aspect of the invention. According to the above-mentioned aspect, similar to the image processing apparatus according to the first aspect, it is possible to estimate the distribution of the object area and the background area in the image which is stored and held as charge in the radiographic image detector when the radiation passing through the object is emitted, before the reading of the image from the radiographic image detector is completed.

Effect of the Invention

As described above, according to the invention, the first leakage current value output through the signal line with a charge corresponding to a uniformly emitted radiation being held in the radiographic image detector is stored, and the ratio between the object area and the background area on the line arranged along the signal line in an image which is stored as charge in the radiographic image detector, or the lengths of the object area and the background area are estimated based on the ratio between the first leakage current value and the second leakage current value output through the signal line, with a charge corresponding to the radiation passing through the object being held in the radiographic image detector, when the radiation passing through an object is emitted to the radiographic image detector. Therefore, it is possible to estimate the distribution of the object area and the background area in the image which is stored and held as charge in the radiographic image detector when the radiation passing through the object is emitted, before the reading of the image from the radiographic image detector is completed.

BRIEF DESCRIPTION OF THE DRAWINGS

FIG. 4 is a diagram schematically illustrating a radiographic image detector and an image reading unit including electrodes.

FIG. 5A is a diagram illustrating a change in charge in a specific unit region.

FIG. 5B is a diagram illustrating a change in leakage current in a specific unit region.

FIG. 6 is a diagram schematically illustrating a target unit region and unit regions affected by a leakage current when charge is read from the target unit region.

FIG. 8A is a diagram illustrating the estimation of the position of the boundary between an object area and a background area in the exemplary image of the breast, which is an object, and shows a CC view.

FIG. 8B is a diagram illustrating the estimation of the position of the boundary between an object area and a background area in the exemplary image of the breast, which is an object, and shows an MLO view.

BEST MODE FOR IMPLEMENTING THE INVENTION

Figure 1:
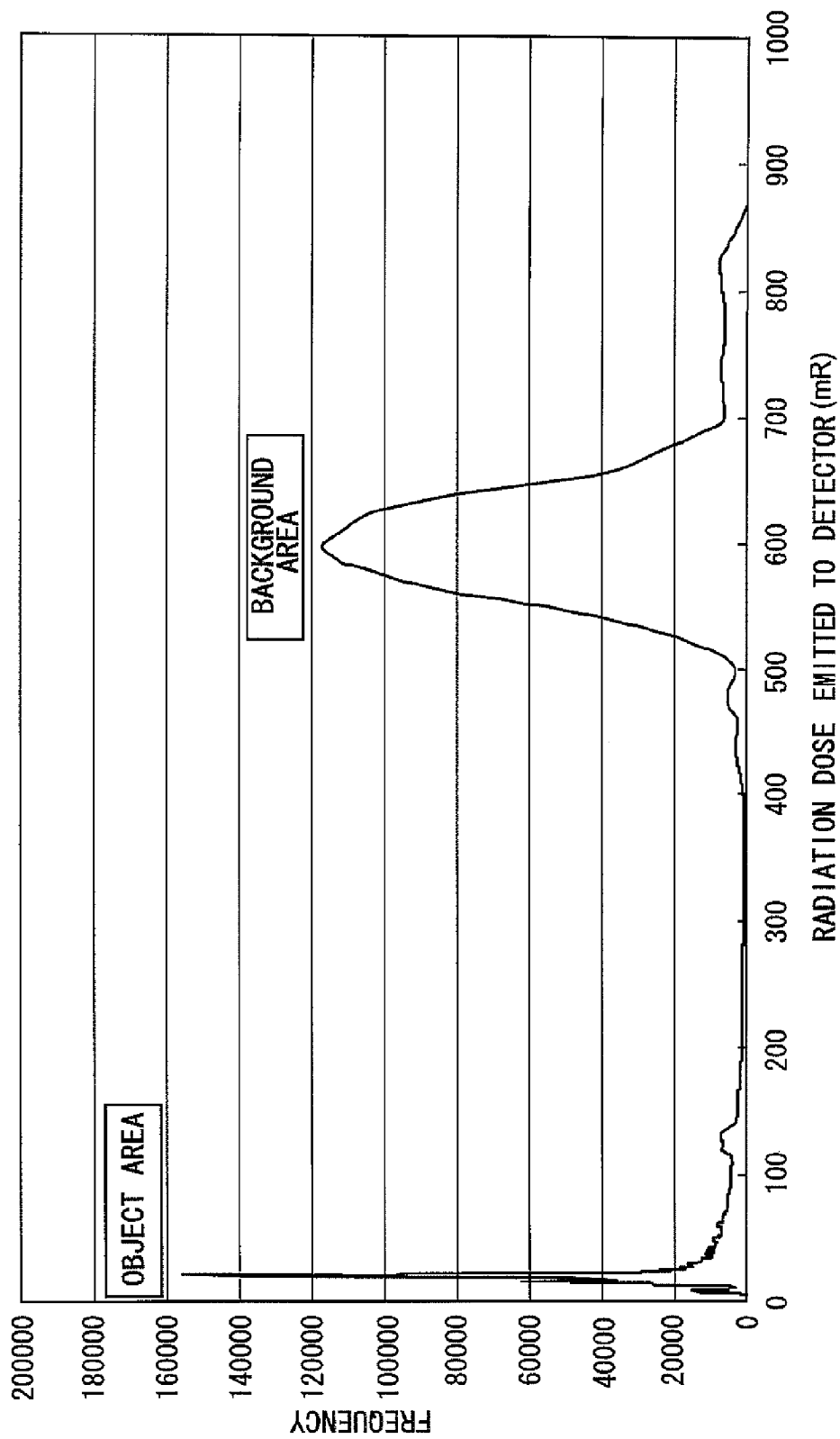
FIG. 1 is a diagram illustrating the results of experiments conducted by the inventors.
Figure 2:
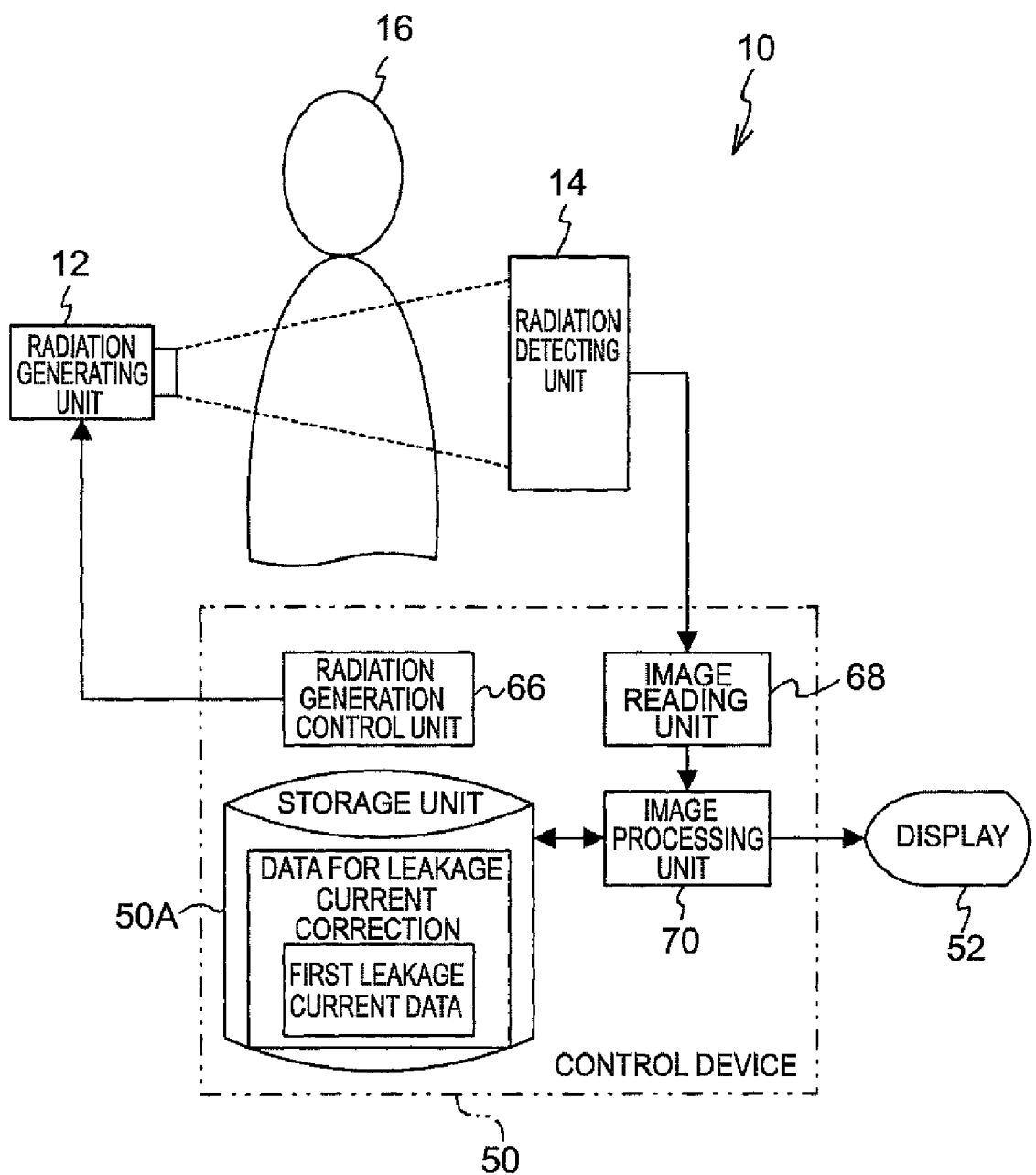
FIG. 2 is a block diagram schematically illustrating the structure of a radiographic imaging apparatus according to an exemplary embodiment of the invention.

Hereinafter, exemplary embodiments of the invention will be described in detail with reference to the accompanying drawings. FIG. 2 shows a radiographic imaging apparatus 10 according to an exemplary embodiment of the invention. The radiographic imaging apparatus 10 includes a radiation generating unit 12 that generates radiation, such as X-rays, and a radiation detecting unit 14 that is provided so as to be separated from the radiation generating unit 12. During an imaging operation, an object 16 is disposed at an imaging position between the radiation generating unit 12 and the radiation detecting unit 14, and the radiation generating unit 12 emits radiation to the object 16 disposed at the imaging position. Then, the radiation passes through the object 16, and the radiation having image information is emitted to the radiation detecting unit 14.

The radiation detecting unit 14 includes a radiographic image detector 20. The radiographic image detector includes an electrostatic recording unit having a photoconductive layer that receives the radiation and has conductivity. The radiographic image detector receives the radiation with the image information, records the image information to the electrostatic recording unit, and outputs an image signal indicating the recorded image information. As the radiographic image detector, any of the following is used: a light-reading-type radiographic image detector that reads the image information recorded on the electrostatic recording unit using a semiconductor material that generates charge when light is emitted; and a radiographic image detector that stores charge generated by irradiation with radiation and reads the stored charge by turning on or off a switching element, such as a thin film transistor (TFT) in each unit region (hereinafter, referred to as a TFT type). Next, an example of the structure of the light-reading-type radiographic image detector will be described.

Figure 3A:
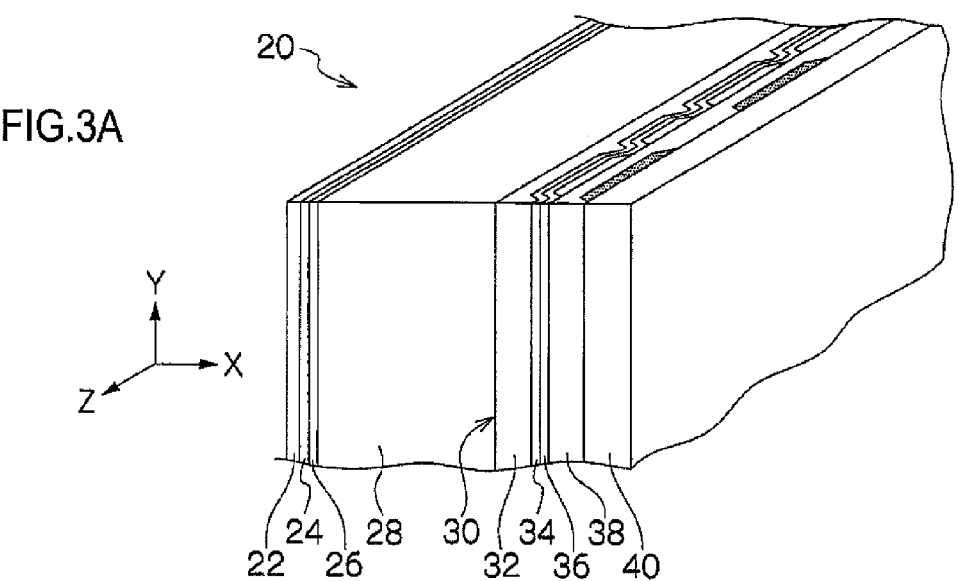
FIG. 3A is a perspective view illustrating a radiographic image detector.
Figure 3B:
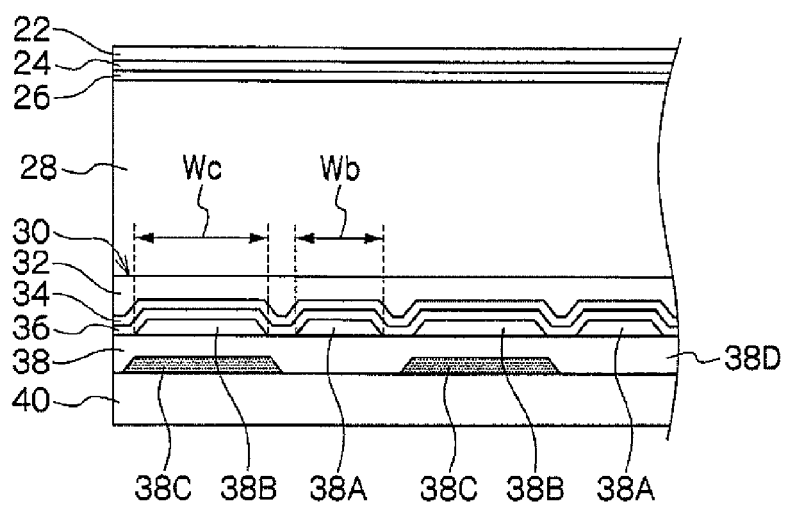
FIG. 3B is a cross-sectional view illustrating the radiographic image detector taken along the line X-Z of FIG. 3A.
Figure 3C:
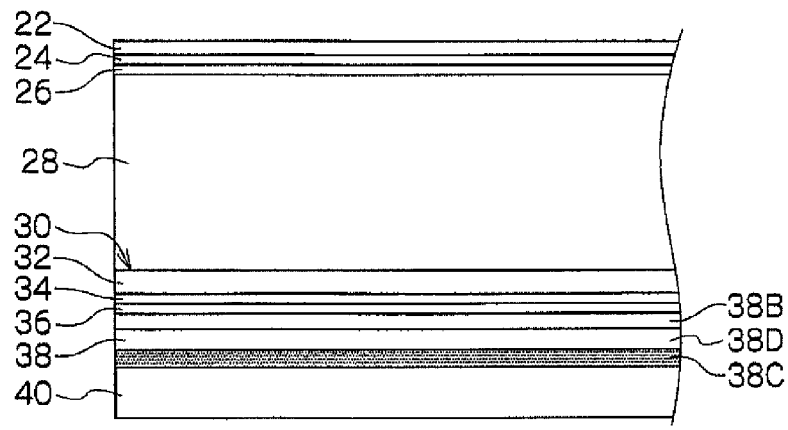
FIG. 3C is a cross-sectional view illustrating the radiographic image detector taken along the line X-Y of FIG. 3A.

As shown in FIGS. 3A to 3C, a light-reading-type radiographic image detector 20 includes a first electrode layer 22 that transmits the radiation (referred to as recording light discriminated from read light, which will be described below) generated by the radiation generating unit 12, a recording photoconductive layer 28 that receives the recording light passing through the first electrode layer 22, generates charge pairs, and has conductivity, a reading photoconductive layer 32 that receives read light, generates charge pairs, and has conductivity, a second electrode layer 38 including a first transparent linear electrode 38A, a second transparent linear electrode 38B, a light shielding film 38C, and an insulating layer 38D, and a substrate 40 that transmits the read light, which are provided in this order. The first transparent linear electrode 38A corresponds to a signal line according to the invention. As shown in FIG. 4, a line light source 54 that emits the read light to the radiographic image detector 20 is provided on one surface of the radiographic image detector 20 close to the substrate 40.

In addition, an electron injection prevention layer 24 that prevents the injection of electrons from the first electrode layer 22 and a crystallization prevention layer 26 that prevents the crystallization of the recording photoconductive layer are provided in this order between the first electrode layer 22 and the recording photoconductive layer 28. A crystallization prevention layer 34 that prevents the crystallization of the reading photoconductive layer 32 and a hole injection prevention layer 36 that prevents the injection of holes from the transparent linear electrodes 38A and 38B when a high voltage is applied are provided in this order between the reading photoconductive layer 32 and the second electrode layer 38. A storage portion 30 that is two-dimensionally arranged and stores a latent image polarity charge with the radiographic image generated from the recording photoconductive layer 28 is formed at the interface between the recording photoconductive layer 28 and the reading photoconductive layer 32.

The size (area) of the radiographic image detector 20 may be equal to or more than, for example, 20 cm×20 cm. In particular, when a breast image is imaged, the effective size of the radiographic image detector 20 may be about 43 cm×43 cm. The hole injection prevention layer 36 may be mainly made of, for example, $CeO_2$ or ZnS. The layer may be a single layer or it may preferably have a multi-layer structure in order to improve capability of preventing hole injection (in order to reduce a dark current). The thickness of the hole injection prevention layer 36 is preferably from 20 nm to 100 nm. The electron injection prevention layer 24 may be made of $Sb_2S_3$ or an organic compound. The electron injection prevention layer 24 may be a single layer or a multi-layer. It is most preferable that the crystallization prevention layers 26 and 307 be made of a binary compound with a high crystallization temperature, such as Se—As, Se—Ge, or Se—Sb, or a ternary compound, such as Se—Ge—Sb, Se—Ge—As, or Se—Sb—As.

The recording photoconductive layer 28 is preferably made of a photoconductive material having a-Se (amorphous selenium) as a main component. It is preferable that the thickness of the recording photoconductive layer 28 be from 50 μm to 1000 μm in order to sufficiently absorb the recording light. It is preferable that the reading photoconductive layer 32 be made of a-Se doped with 10 to 200 ppm of Cl having a large difference between the mobility of a negative charge of the first electrode layer 22 and the mobility of a positive charge opposite to the negative charge, or a photoconductive material having Se as a main component such as Se—Ge, Se—Sb, or Se—As. It is preferable that the thickness of the reading photoconductive layer 32 be equal to or less than half of the thickness of the recording photoconductive layer 28. In addition, as the thickness of the reading photoconductive layer 32 is reduced, responsiveness during reading is improved. Therefore, the thickness of the reading photoconductive layer 32 is preferably equal to or less than 1/10, more preferably, 1/100 of the thickness of the recording photoconductive layer 28.

The materials forming the above-mentioned layers are just an example that is suitable when the first electrode layer 22 is charged with a negative charge, the transparent linear electrodes 38A and 38B of the second electrode layer 38 is charged with a positive charge, the negative charge, which is a latent image polarity charge, is stored in the storage portion 30 that is formed at the interface between the recording photoconductive layer 28 and the reading photoconductive layer 32, and the reading photoconductive layer 32 serves as a so-called hole transport layer in which the mobility of the negative charge, which is the latent image polarity charge, is less than the mobility of the positive charge, which is a transport polarity charge, opposite to the negative charge. The polarities of the charges may be reversed. When the polarities are reversed, a little change in structure is required. For example, a reading photoconductive layer, serving as a hole transport layer, is changed to a reading photoconductive layer, serving as an electron transport layer. In addition, the reading photoconductive layer 32 may be made of a material having a-Se as a main component and the storage portion 30 may be an $As_2Se_3$, GeSe, $GeSe_2$, or $Sb_2Se_3$ layer.

Each of the first electrode layer 22 and the first transparent linear electrode 38A may transmit the recording light or the read light. For example, when the layers transmit visible rays, they may be made of a metal oxide, such as $SnO_2$, ITO (Indium Tin Oxide), or IZO (Indium Zinc Oxide), which has been known as a material forming a light transmissive metal oxide thin film, or IDIXO (Indium X-Metal Oxide; manufactured by Idemitsu Kosan Co., Ltd.), which is an amorphous light transmissive metal oxide that is easily etched, with a thickness of about 50 to 200 nm, preferably, a thickness of equal to or more than 100 nm. When X-rays are used as the recording light and the X-rays are emitted from the first electrode layer 22 to record a radiographic image, the first electrode layer 22 does not need to transmit visible light. Therefore, the first electrode layer 22 may be made of pure metal, such as Al or Au, with a thickness of 100 nm.

The second transparent linear electrodes 38B of the second electrode layer 38 are arranged in a stripe shape at a unit region pitch, and the unit region pitch may be in the range of about 50 μm to 250 μm in order to obtain a high S/N ratio while maintaining high sharpness in medical radiography. In the range of the unit region pitch, the width of the second transparent linear electrode 38B may be in the range of about 10 μm to 200 μm. The first transparent linear electrode 38A of the second electrode layer 38 is provided as a conductive member for outputting an electric signal with a level corresponding to the amount of latent image polarity charge stored in the storage portion 30 which is formed at the interface between the recording photoconductive layer 28 and the reading photoconductive layer 32, and is arranged in a stripe shape, similar to the second transparent linear electrode 38B. When the electrodes of the second electrode layer 38 are formed in a stripe shape, it is possible to simply correct structure noise or reduce capacitance. Therefore, it is possible to improve the S/N ratio of an image or reduce a read time by performing parallel reading (mainly in the main scanning direction).

The second transparent linear electrodes 38B and the first transparent linear electrodes 38A of the second electrode layer 38 are alternately arranged in parallel with each other. It is preferable that the above-mentioned light transmissive metal oxide thin film be used as the second transparent linear electrode 38B. In this case, it is possible to pattern the first transparent linear electrode 38A and the second transparent linear electrode 38B with one lithography process. In this case, the light shielding film 38C made of a material with low light transmittance is provided on a portion of the substrate 40 corresponding to each of the second transparent linear electrodes 38B such that the radiation intensity of read light to the second transparent linear electrode 38B is lower than that of read light to the first transparent linear electrode 38A. In this way, the transmittance Pc of the read light may be equal to or less than 10%, that is, a light shielding property may be obtained. It is possible to prevent charge pairs for reading signals from being generated in a portion of the reading photoconductive layer 32 corresponding to the second transparent linear electrodes 38B. Then, the hole injection prevention layer 36, which is a thin film with a thickness of equal to or less than 100 nm, is formed on the first transparent linear electrodes 38A and the second transparent linear electrodes 38B. In addition, each first transparent linear electrode 38A and each second transparent linear electrode 38B are spaced a predetermined distance from each other such that they are electrically insulated.

In the radiographic image detector 20, it is preferable that the width Wc of the second transparent linear electrode 38B be more than the width Wb of the first transparent linear electrode 38A and the transmittance Prb of the first transparent linear electrode 38A with respect to the read light and the transmittance Prc of the second transparent linear electrode 38B with respect to the read light satisfy the following conditional expression: (Wb×Prb)/(Wc×Prc)≧5. In this case, when the width Wc of the second transparent linear electrode 38B is more than the width Wb of the first transparent linear electrode 38A, during the recording of an electrostatic latent image, the first transparent linear electrode 38A and the second transparent linear electrode 38B are connected to each other and the second transparent linear electrode 38B is actively used to form an electric field distribution. As such, when the first transparent linear electrode 38A and the second transparent linear electrode 38B are connected to each other for recording, the latent image polarity charge is stored at a position corresponding to the second transparent linear electrode 38B in addition to a position corresponding to the first transparent linear electrode 38A. When read light is emitted to the reading photoconductive layer 32 through the first transparent linear electrode 38A during reading, the latent image polarity charge above two second transparent linear electrodes 38B interposing the first transparent linear electrode 38A therebetween is sequentially read through the first transparent linear electrode 38A. Therefore, in this case, a position corresponding to the first transparent linear electrode 38A is the center of a unit region, and about half of each of the two second transparent linear electrodes 38B interposing the first transparent linear electrode 38A therebetween is one unit region in the direction in which the first transparent linear electrode 38A and the second transparent linear electrode 38B are parallel with each other. It is preferable that a conductive member having conductivity that is more than those of the first transparent linear electrode 38A and the second transparent linear electrode 38B be used as a bus line and the bus line extend for each first transparent linear electrode 38A and each second transparent linear electrode 38B in the lengthwise direction thereof.

The light shielding film 38C is not necessarily made of an insulating material, but it may be made of a material for allowing the specific resistance of the light shielding film 38C to be equal to or more than $2\times10^{-6}$ Ω·cm (preferably, equal to or less than $1\times10^{15}$ Ω·cm). For example, the light shielding film 38C may be made of a metal material, such as Al, Mo, or Cr, or an inorganic material, such as $MoS_2$, $WSi_2$, or TiN. It is preferable to use a material for allowing the specific resistance of the light shielding film 38C to be equal to or more than 1 Ω·cm. When the light shielding film 38C is made of a conductive material such as a metal material, an insulating member is interposed between the light shielding film 38C and the second transparent linear electrode 38B in order to prevent direct contact therebetween. In the radiographic image detector 20 according to this exemplary embodiment, as the insulating member, an insulating layer 38D made of, for example, $SiO_2$ is provided between the reading photoconductive layer 32 and the substrate 40. The thickness of the insulating layer 38D is preferably in the range of about 0.01 μm to 10 μm. During the formation of the light shielding film 38C, when the radiation intensity of read light to the first transparent linear electrode 38A is Ub and the radiation intensity of read light to the second transparent linear electrode 38B is Uc, it is preferable that the thickness of the light shielding film 38C be set so as to satisfy Ub/Uc≧5. In the above-mentioned expression, the right side is preferably 8, more preferably, 12.

When the gap between the first transparent linear electrode 38A and the second transparent linear electrode 38B is Wbc, it is preferable that the width Wd of the light shielding film 38C satisfy Wc≦Wd≦(Wc+2×Wbc). This conditional expression indicates that the light shielding film 38C completely covers at least the second transparent linear electrode 38B, a portion of the light shielding film that transmits read light and has a width that is equal to at least the width Wb of the first transparent linear electrode 38A is ensured, and the light shielding film 38C is not provided on a portion corresponding to the first transparent linear electrode 38A. However, when the width of the light shielding film is equal to the width Wc of the second transparent linear electrode 38B, it is difficult to sufficiently shield light. In addition, when the width of a portion that transmits the read light is equal to the width Wb of the first transparent linear electrode 38A, an insufficient amount of read light reaches the first transparent linear electrode 38A. Therefore, it is preferable that the width Wd of the light shielding film satisfy (Wc+Wbc/2)≦Wd≦ (Wc+Wbc).

The radiographic image detector 20 corresponds to a radiographic image detector according to the invention.

As shown in FIG. 2, the radiation generating unit 12 and the radiation detecting unit 14 are connected to a control device 50. The control device 50 includes a computer including a CPU, a memory, such as a RAM, and a non-volatile storage unit 50A, such as an HDD (hard disk drive) (components other than the storage unit 50A are not shown), and a peripheral circuit connected to the computer. When a predetermined program stored in the storage unit 50A is executed by the CPU of the computer, the computer and the peripheral circuit cooperate with each other to function as a radiation generation control unit 66 that controls the generation of radiation by the radiation generating unit 12 and an image reading unit 68 that reads image information from the radiographic image detector 20. In addition, a display 52 that displays a radiographic image is connected to the control device 50.

As shown in FIG. 4, the image reading unit 68 includes the line light source 54. The line light source 54 is formed by arranging plural LEDs (for example, LEDs that emit B light) in the direction (main scanning direction) in which the first transparent linear electrodes 38A (and the second transparent linear electrodes 38B) are arranged in the radiographic image detector 20. When image information is read from the radiographic image detector 20, each of the LEDs is turned on by a driving circuit (not shown), which is a part of the image reading unit 68, and linear read light is radiated to one surface of the radiographic image detector 20 close to the substrate 40. The line light source 54 is supported by a moving mechanism (not shown), which is a part of the image reading unit 68, so as to be movable on the surface of the radiographic image detector 20 close to the substrate 40 along the direction in which the first transparent linear electrodes 38A extend (a sub-scanning direction (read direction): the direction of an arrow A in FIG. 4). When image information is read from the radiographic image detector 20, the line light source 54 is moved (sub-scanned) by the moving mechanism in the sub-scanning direction at a constant movement speed. In this way, linear read light is sequentially radiated to the entire surface of the radiographic image detector 20 close to the substrate 40.

The image reading unit 68 includes plural charge amplifiers 56 that are connected to different first transparent linear electrodes 38A of the radiographic image detector 20, a high voltage power supply 58 that applies a high voltage between the individual first transparent linear electrode 38A and the first electrode layer 22 through the charge amplifiers 56 (since the potential between two input terminals of each of the charge amplifiers 56 is equal when a power supply is turned on) when radiation is emitted to the radiographic image detector 20, a multiplexer (MPX) 60 that is connected to the output terminals of the charge amplifiers 56 and selectively outputs electric signals input from the charge amplifiers 56, and an A/D converter 62 that is connected to an output terminal of the multiplexer 60, converts the electric signal input from the multiplexer 60 into digital data, and outputs the digital data.

In the radiographic image detector 20, in the state in which the application of a high voltage from the high voltage power supply 58 stops, the first electrode layer 22 is connected to the high voltage power supply, and the second electrode layer 38 is connected to the ground, when linear read light is emitted from the line light source 54, among the image information recorded on the radiographic image detector 20 as the latent image polarity charge stored in the storage portion 30, image information corresponding to one line that is recorded on a portion irradiated with the read light is output as an electric signal with a level corresponding to the amount of latent image polarity charge to each unit region through the individual first transparent linear electrode 38A. The multiplexer 60 sequentially switches the electric signals to be output to the A/D converter 62 such that the electric signals that have been output from the individual first transparent linear electrodes 38A and then amplified by the charge amplifiers 56 are sequentially output to the A/D converter 62. In this way, the A/D converter 62 sequentially outputs image data corresponding to one line. While the linear read light is emitted from the light line light source 54 to the entire surface of the radiographic image detector 20 close to the substrate 40, the above-mentioned process is repeatedly performed to read as image data image information corresponding to one image surface which is recorded on the radiographic image detector 20.

An image processing program is also stored in the storage unit 50A of the control device 50. When the image processing program is executed by the CPU, the control device 50 functions as an image processing unit 70 shown in FIG. 2. The image processing unit 70 implemented by executing the image processing program corresponds to an image processing apparatus according to the invention. The image processing program includes an image reading program for executing an image reading process, which will be described below, and a leakage current correcting program for preview that executes a leakage current correcting process for preview, which will be described below. The image reading program and the leakage current correcting program for preview correspond to an image processing program according to the invention. The storage unit 50A also stores leakage current correcting data that is used to correct a leakage current.

Next, the operation of this exemplary embodiment will be described. FIG. 5A shows a change in the charge (latent image polarity charge) stored and held in each unit region of the radiographic image detector 20. As shown in FIG. 5A, the amount of change in each unit region of the radiographic image detector 20 is set to 0 as quickly as possible. However, when a radiation with image information is emitted with the high voltage power supply 58 applying a high voltage, the amount of charge corresponding to the radiation dose is generated in the recording photoconductive layer 28, and the charge is stored and held in each unit region. When the application of a high voltage from the high voltage power supply 58 stops in order to read an image from the radiographic image detector 20, the first electrode layer 22 is connected to the high voltage power supply, and the second electrode layer 38 is connected to the ground, the charge is stored in the storage portion 30. In this case, a leakage current that is gradually attenuated over time is generated in each unit region (see FIG. 5B), and the leakage current superimposes a read current when the charge in another unit region is read. The amount of charge stored and held in each unit region is gradually reduced with the generation of the leakage current. When image reading is performed to read charge from a specific unit region from which charge has not been read, the amount of charge in the specific unit region is 0, and the leakage current in the specific unit region is also 0.

As described above, the leakage current is generated from each unit region of the radiographic image detector 20 during the period from the time when the application of a high voltage stops to the time when the charge stored and held in each unit region is read. The leakage current generated from each unit region superimposes the read current flowing through the second transparent linear electrode 38 corresponding to each unit region, among the plural second transparent linear electrodes 38 provided in the radiographic image detector 20. Therefore, as shown in FIG. 6, when the charge stored in a specific unit region (in FIG. 6, a 'target unit region') is read through the second transparent linear electrode 38, the read current superimposes the leakage current from a unit region that is disposed on the same signal line as a specific unit region along the movement direction (sub-scanning direction) of the line light source 54 (that corresponds to the same second transparent linear electrode 38 as that in the specific unit region) and is in a non-charge-read state when the charge in the specific unit region is read, among the unit regions of the radiographic image detector 20. In FIG. 6, each unit region is represented by '□'. However, '□' schematically indicates the position of each unit region, and it is noted that the position of each unit region from which the charge is read is not necessarily identical to the range indicated by '□'.

Therefore, when the image reading unit 68 completely reads an image from the radiographic image detector 20 and image data corresponding to one surface is completely input, the image processing unit 70 estimates, from the input image data, the leakage current that superimposes the read current for reading charge from a specific unit region and that flows from each unit region which is disposed on the same signal line as the specific unit region and which is in a non-charge-read state when the charge in the specific unit region is read. Then, the image processing unit 70 performs a leakage current correcting process to correct the data of each specific unit region according to the leakage current from each individual unit region for which current has been estimated, for all the unit regions of the image. In this way, it is possible to obtain image data indicating a high-resolution radiographic image (image for diagnosis) without the image being affected by a leakage current that superimposes with a read current.

In the leakage current correction, the leakage current from each unit region may be estimated by the following Expression 1:

$$\text{Leakage current} = A\exp(-\alpha t) \quad \text{Expression 1}$$

In Expression 1, t indicates the time elapsed from when application of a high voltage to the radiographic image detector 20 is stopped to when a charge is read from a unit region to be corrected; A indicates a coefficient that depends on the amount of charge read from a unit region which is a leakage current estimation object, and a indicates a time constant. As can be seen from Expression 1, in order to estimate the leakage current, it is necessary to know the amount of charge stored in a unit region that is a leakage current estimation object. Therefore, the correction of the leakage current should be performed after image reading is completed. In contrast, a preview image displayed on the display 52 before a diagnostic image is displayed is used by the operator to determine whether an imaging range or a captured image is appropriate. Therefore, while the accuracy of the preview image does not need to be as high as that of the diagnostic image, the preview image needs to be displayed on the display 52 as quickly as possible.

Figure 7A:
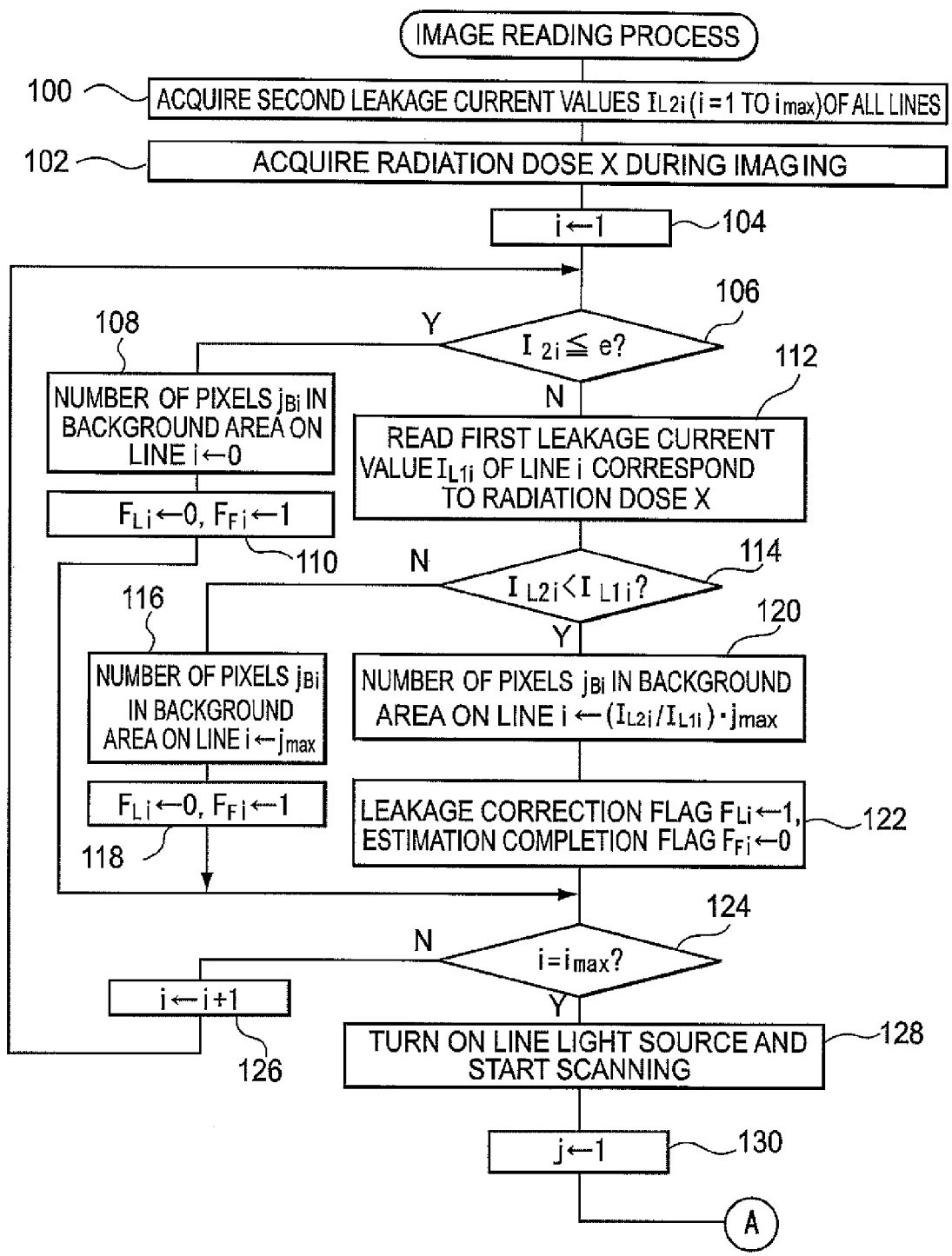
FIG. 7A is a flowchart illustrating the content of an image reading process.
Figure 7B:
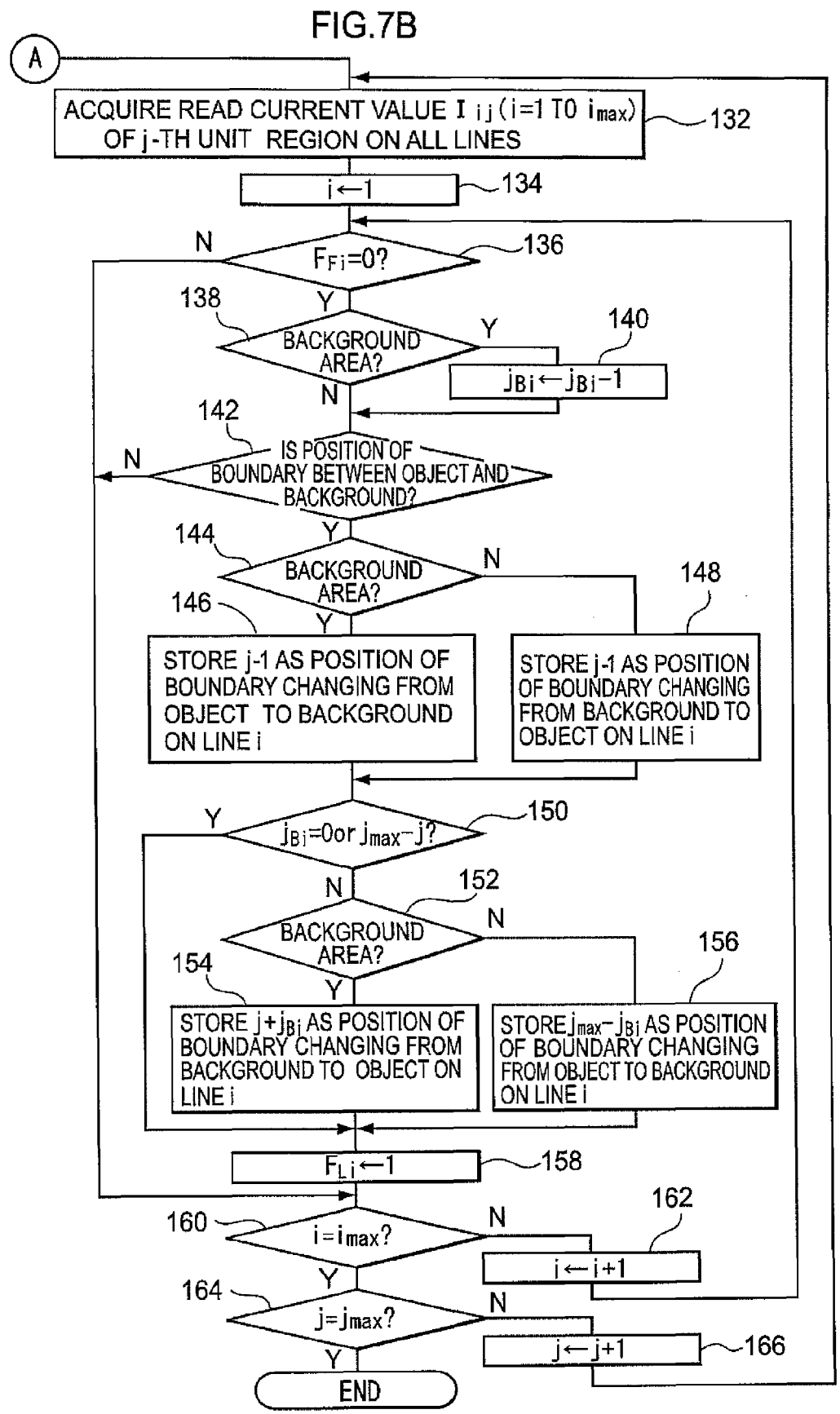
FIG. 7B is a flowchart illustrating the content of the image reading process.
Figure 9A:
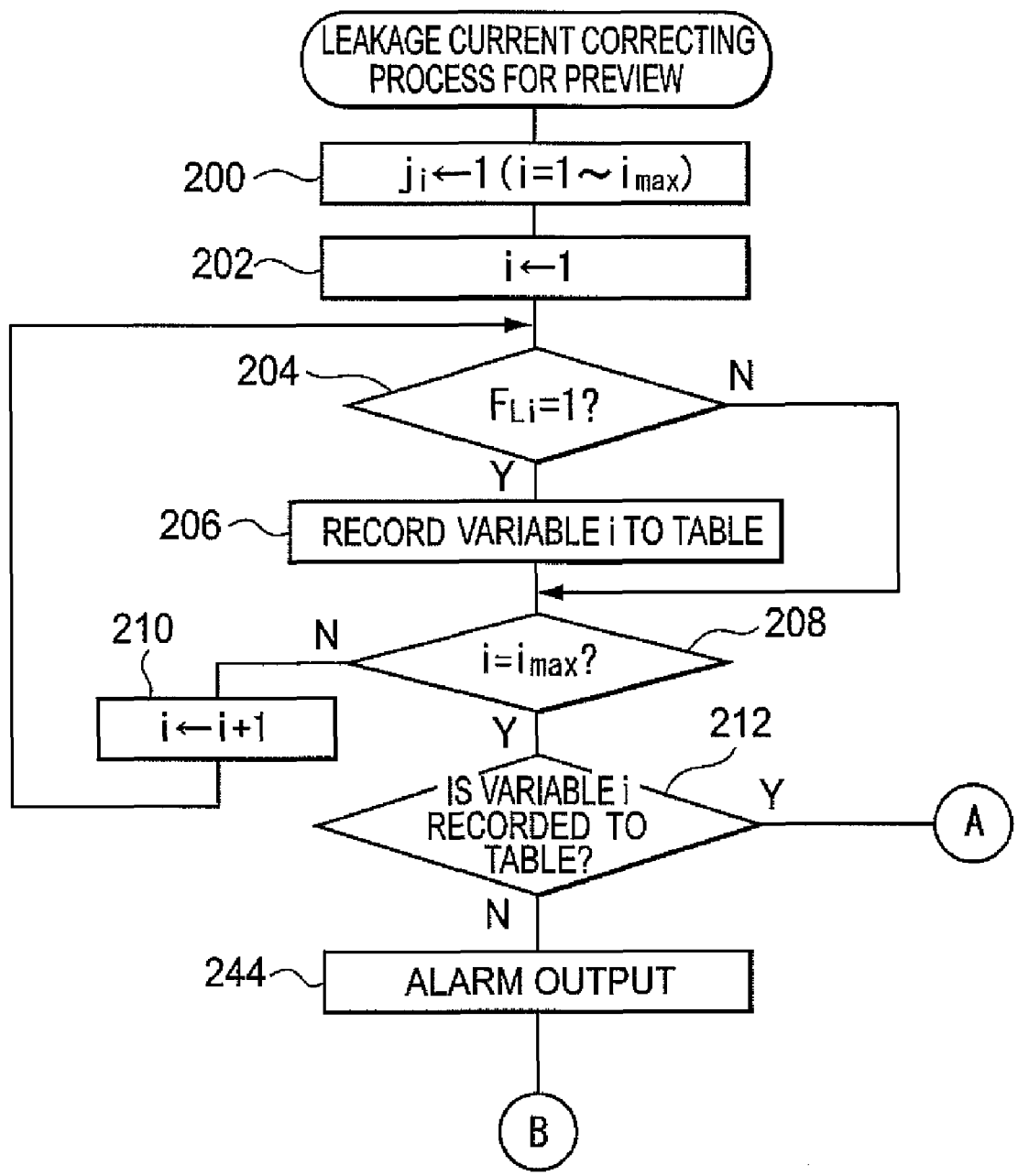
FIG. 9A is a flowchart illustrating the content of a leakage current correcting process for preview.
Figure 9B:
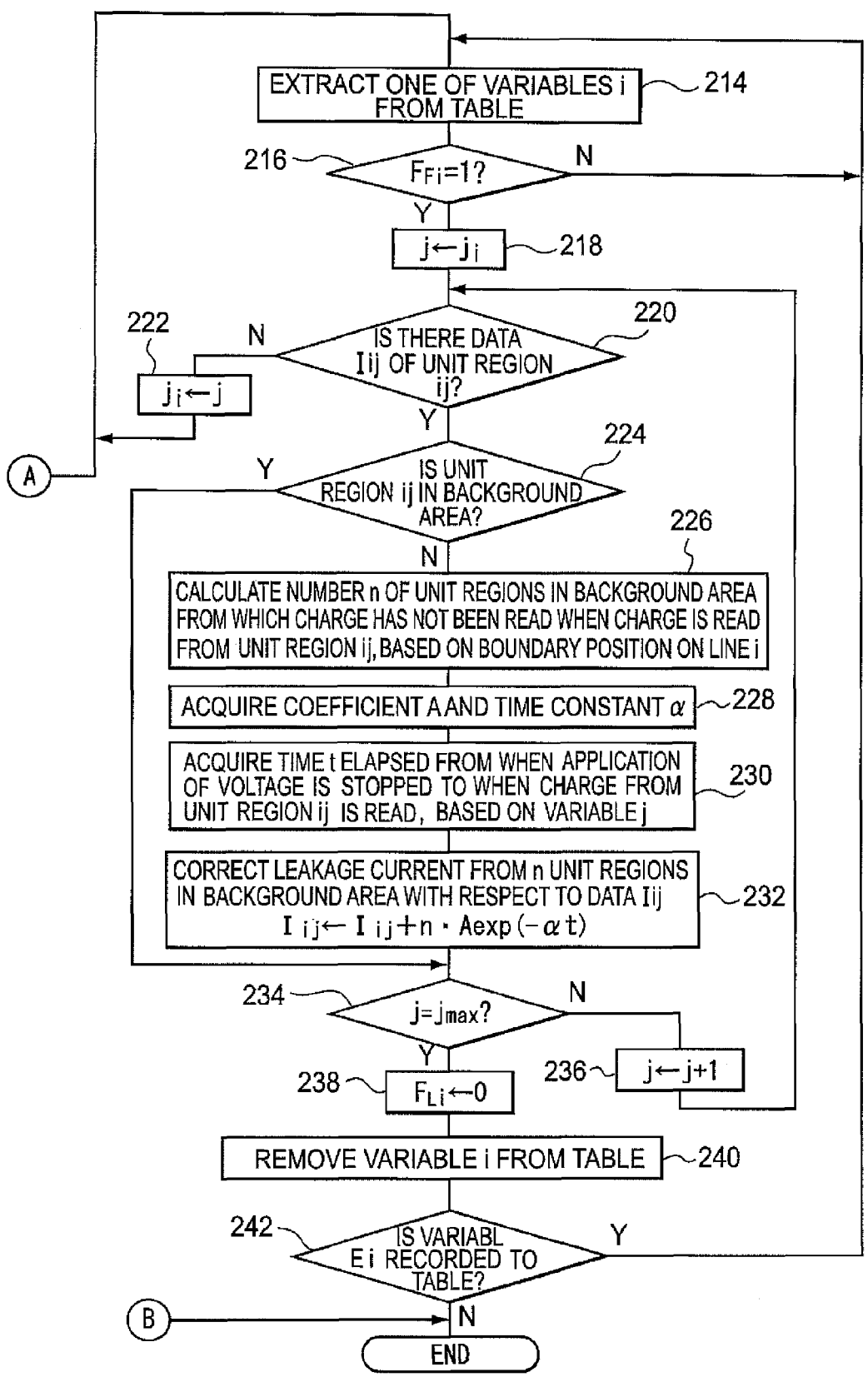
FIG. 9B is a flowchart illustrating the content of the leakage current correcting process for preview.

Therefore, the image processing unit 70 according to this exemplary embodiment performs the image reading process shown in FIGS. 7A and 7B to read an image from the radiographic image detector 20, and performs the leakage current correcting process for preview shown in FIGS. 9A and 9B in parallel with the image reading process to obtain image data for a preview image. Next, the image reading process performed when the radiographic imaging apparatus 10 images the imaged object 16 will be described with reference to FIGS. 7A and 7B. In addition, an example in which a breast is imaged as the imaged object 16 will be described below.

In the image reading process, first, in Step 100, when the object 16 is imaged, the radiation passing through the object 16 is emitted to the radiographic image detector 20 and a charge corresponding to the radiation dose is stored in each unit region of the radiographic image detector 20. In this state, data is acquired indicating the amount (a second leakage current value $I_{L2i}$ (where i=1 to imax, and imax indicates the total number of lines: see FIGS. 8A and 8B)) of leakage current output from each line (second transparent linear electrode 38) of the radiographic image detector 20 through the charge amplifiers 56, the multiplexer 60, and the A/D converter 62 of the image reading unit 68, with the line light source 54 turned off (a read light is not emitted), and the acquired data is stored in the memory. In Step 102, the radiation dose X emitted to the imaged object 16 during imaging is acquired and a variable i is set to 1 in Step 104.

In Step 106, it is determined whether the second leakage current value $I_{2i}$ of a line i stored in the memory is equal to or less than a predetermined value e. As the predetermined value e, for example, the following value may be used: a value corresponding to the leakage current when the unit region belonging to a background area of the image does not exist on the line i, more specifically, it may be a value corresponding to a read current when the radiation dose is approximately 0.1 mR. If the determination result is 'Yes', a unit region belonging to the background area of the image does not exist on the line i (all of the unit regions in a unit region group corresponding to the line i belong to an object area of the image), and it is determined that there is no boundary between the object area and the background area on the line i. As a result, the process proceeds to Step 108 and the number of pixels $j_{Bi}$ in the background area that are on the line i is set to 0. In Step 110, a leakage correction flag $F_{Li}$ indicating whether the line i is a leakage current correction object, is set to 0, which indicates that it is not an object of correction, and an estimation completion flag $F_{Fi}$, indicating whether the boundary position on the line i needs to be estimated (or whether estimation of the boundary position on the line i has been completed), is set to 1, which indicates that estimation is not required. Subsequently, the process proceeds to Step 124.

If the determination result in Step 106 is 'No', it is determined that a unit region belonging to the background area of the image exists on the line i. Therefore, the process proceeds to Step 112. In this exemplary embodiment, a process of uniformly emitting a predetermined radiation dose to the entire surface of the radiographic image detector 20 and acquiring data indicating the amount (first leakage current value $I_{L1i}$) of leakage current output from each line of the radiographic image detector 20 is performed plural times with different radiation doses to obtain plural first leakage current values $I_{L1i}$ (first leakage current values $I_{L1i}$ corresponding to different radiation doses) for each line. The first leakage current values $I_{L1i}$ are stored as a portion of leakage current correcting data in the storage unit 50A. Therefore, the storage unit 50A corresponds to a storage unit according to the invention. In Step 112, among the plural first leakage current values $I_{L1i}$ of the line i stored in the storage unit 50A, the first leakage current value $I_{L1i}$ corresponding to the radiation dose X obtained in Step 102 is read from the storage unit 50A. In Step 114, it is determined whether the second leakage current value $I_{L2i}$ of the line i is less than the first leakage current value $I_{L1i}$ read in Step 112.

Since radiation is uniformly emitted to the entire surface of the radiographic image detector 20 in order to acquire the first leakage current value $I_{L1i}$, each unit region of the radiographic image detector 20 has an amount of charge corresponding to the background area of a normal image. Therefore, if the determination result in Step 114 is 'No' (if the second leakage current value $I_{L2i}$ is equal to the first leakage current value $I_{L1i}$), all of the unit regions in a unit region group corresponding to the line i belong to the background area of the image (for example, see line A shown in FIG. 8A and line B shown in FIG. 8B), and it is determined that there is no boundary between the object area and the background area on the line i. Therefore, the process proceeds to Step 116, and jmax (see FIGS. 8A and 8B) indicating the total number of pixels (the total number of unit regions on one line) on the line i is set to the number of pixels $j_{Bi}$ in the background area. Then, in Step 118, the leakage correction flag $F_{Li}$ of the line i is set to 0 (representing an object that is not to be corrected), and the estimation completion flag $F_{Fi}$ of the line i is set to 1 (indicating that estimation is not required). Then, the process proceeds to Step 124.

If the determination result in Step 106 is 'No' and the determination result in Step 114 is 'Yes', the second leakage current value $I_{L2i}$ of the line i is more than the predetermined value e and is less than the first leakage current value $I_{L1i}$ of the line i. Therefore, a unit region group corresponding to the line i includes unit regions belonging to the object area, as well as unit regions belonging to the background area of the image (for example, see line B shown in FIG. 8A and lines D and E shown in FIG. 8B), and it is determined that there is a boundary between the object area and the background area on the line i. If the determination result in Step 114 is 'Yes', the process proceeds to Step 120, and the number of pixels $j_{Bi}$ in the background area on the line i is estimated as the length of the background area on the line i, based on the ratio ($I_{L2i}/I_{L1i}$) of the second leakage current value $I_{L2i}$ to the first leakage current value $I_{L1i}$ on the line i, according to the following Expression 2:

$$j_{Bi}=(I_{L2i}/I_{L1i}) \cdot j\max \qquad \text{Expression 2}$$

In Expression 2, it is assumed that the leakage current from the unit region belonging to the area of the imaged object in the unit region group corresponding to the line i is zero. However, the number of pixels in the background area on the line i $j_{Bi}$ may be estimated by Expression 3 instead of Expression 2, which considers that the leakage current from the unit region belonging to the object area may be a very small value but not zero:

$$j_{Bi}=((I_{L2i}-e)/(I_{L1i}-e)) \cdot j\max \qquad \text{Expression 3}$$

In Expression 3, instead of using a predetermined fixed value as the predetermined value e, a measured value (for example, a leakage current value obtained when a radiation of about 0.1 mR is uniformly emitted to the entire surface of the radiographic image detector 20) may be used as the predetermined value e. In Step 122, the leakage correction flag $F_{Li}$ of the line i is set to 1, which indicates it is an object of correction, and the estimation completion flag $F_{Fi}$ of the line i is set to 0, which indicates that estimation of a boundary position has not been completed.

When the number of pixels $j_{Bi}$ in the background area on the line i, the leakage correction flag $F_{Li}$, and the estimation completion flag $F_{Fi}$ are set as described above, it is determined in Step 124 whether the variable i has reached the total number of lines $i_{max}$. If the determination result is 'No', the variable i is increased by 1 in Step 126, and the process returns to Step 106. Steps 106 to 126 are repeatedly performed until the determination result in Step 124 is 'Yes'. In this way, the number of pixels in the background area on the line i $j_{Bi}$, the leakage correction flag $F_{Li}$, and the estimation completion flag $F_{Fi}$ are set for each of the lines of the radiographic image detector 20.

If the determination result in Step 124 is 'Yes', the process proceeds to Step 128. From Step 128, a process of estimating the position of the boundary between the object area and the background area on the line having the estimation completion flag $F_{Fi}$ set to 0 is performed while reading an image from the radiographic image detector 20. That is, in Step 128, the line light source 54 is turned on to emit reading light to the radiographic image detector 20, and the line light source 54 is moved (sub-scanned) in the sub-scanning direction by the moving mechanism (not shown), thereby reading the image from the radiographic image detector 20. In Step 130, the variable j is set to 1. In Step 132, data indicating the amount of a read current (read current value $I_{ij}$) output from each line of the radiographic image detector 20 according to the amount of charge stored in a j-th unit region from the upstream side in the read direction of each line is acquired through the charge amplifiers 56, the multiplexer 60, and the A/D converter 62 of the image reading unit 68, and the acquired data is stored in the memory.

In Step 134, the variable i is set to 1. In Step 136, it is determined whether the estimation completion flag $F_{Fi}$ of the line i is 0. If the determination result is 'No', it is determined that the estimation of the boundary position on the line i is not needed, and the process proceeds to Step 160. If the determination result in Step 136 is 'Yes', the process proceeds to Step 138, and referring to the read current value $I_{ij}$ of a j-th unit region from the upstream side in the read direction of the line i (hereinafter, this unit region may be referred to as "unit region (i, j)"), it is determined whether the unit region (i, j) belongs to the background area of the image. If the determination result is 'No', the process proceeds to Step 142. On the other hand, if the determination result in Step 138 is 'Yes', the number of pixels $j_{Bi}$ in the background area on the line i is decreased by 1 in Step 140, and the process proceeds to Step 142. While the image is read from the radiographic image detector 20, the number of pixels $j_{Bi}$ in the background area on the line i is decreased by 1 in Step 140 whenever a unit region from which the held charge is newly read as a current in the unit region group corresponding to the line i is determined to belong to the background area. Therefore, the number of pixels $j_{Bi}$ in the background area on the line i indicates the length (the number of pixels) of the background area within the range of the line i for which charge has not yet been read.

In Step 142, it is determined whether the difference between the read current value $I_{ij}$ of the unit region (i, j) and the read current value $I_{ij-1}$ of the unit region (i, j–1) is equal to or more than the predetermined value, thereby determining whether the boundary between the object area and the background area of the image is disposed between the unit region (i, j) and the unit region (i, j–1). When the variable j is 1, there is no unit region (i, j–1). Therefore, this is unconditionally determined, and the process proceeds to Step 160. In Step 160, it is determined whether the variable i has reached the total number of lines imax. If the determination result is 'No', the variable i is increased by 1 in Step 162, and the process returns to Step 136. Then, steps 136 to 162 are repeatedly performed until the determination result in Step 160 is 'Yes'. In this way, for those lines having an estimation completion flag $F_{Fi}$ set to 0 of the lines of the radiographic image detector 20, when the j-th unit region (i, j) thereof belongs to the background area, the number of pixels $j_{Bi}$ in the background area is decreased by 1, and the process of determining whether the boundary between the object area and the background area is disposed between the unit region (i, j) and the unit region (i, j–1) is performed with respect to each line.

When the above-mentioned process is performed on each line and the determination result in Step 160 is 'Yes', the process proceeds to Step 164 to determine whether the variable j has reached the total number of pixels jmax (the total number of unit regions) of one line. If the determination result is 'No', the variable j is increased by 1 in Step 166 and the process returns to Step 132. In this way, a process of reading the charge held in a unit region from which charge has not been read for each line as a current and acquiring the read current value (data indicating the read current value $I_{ij}$) (Step 132) is sequentially performed on the unit regions arranged in the sub-scanning direction, and Steps 136 to 162 are performed on each line whenever a new read current value $I_{ij}$ (data indicating the new read current value $I_{ij}$) is acquired.

A boundary between the object area and the background area may exist on the line i having an estimation completion flag $F_{Fi}$ initially set to 0, such as line B shown in FIG. 8A or lines D and E shown in FIG. 8B, and when the read current value $I_{ij}$ of the unit region (i, j) corresponding to the boundary is acquired in Step 132, the determination result in Step 142 becomes 'Yes', and the process proceeds to Step 144 to determine whether the unit region (i, j) whose read current value $I_{ij}$ is acquired belongs to the background area of the image.

If the determination result in Step 142 is 'Yes', the boundary between the object area and the background area is disposed between the unit region (i, j) and the unit region (i, j–1) on the line i. When the unit region (i, j) belongs to the background area, the unit region (i, j–1) belongs to the object area, and it is determined that the position of the boundary between the unit region (i, j) and the unit region (i, j–1) changes from the object area to the background area in the direction (sub-scanning direction) in which image data is read. Therefore, if the determination result in Step 144 is 'Yes', the process proceeds to Step 146 and a value (j–1), obtained by subtracting 1 from the variable j, is stored in the memory as the position of a boundary that changes from the object area to the background area on the line i. When the unit region (i, j) belongs to the object area and the unit region (i, j–1) belongs to the background area, it is determined that the position of the boundary between the unit region (i, j) and the unit region (i, j–1) changes from the background area to the object area in the direction (sub-scanning direction) in which image data is read. Therefore, if the determination result in Step 144 is 'No', the process proceeds to Step 148 and the value (j–1), obtained by subtracting 1 from the variable j, is stored in the memory as the position of a boundary that changes from the background area to the object area on the line i.

In general, when a breast is imaged as the imaged object 16, in order to perform an accurate diagnosis, an imaging method (such as an imaging direction or the approximate range of the object area in the image) is predetermined, and a captured image is a CC view shown in FIG. 8A or an MLO view shown in FIG. 8B. Therefore, as can be seen from FIGS. 8A and 8B, the maximum value of the number of boundaries between the object area and the background area on each line in the captured image is 2, and the minimum value thereof is 0. There are one or more boundaries between the object area and the background area on a line i which has its estimation completion flag $F_{Fi}$ initially set to 0, and for which 'Yes' has been determined in Step 136. When one boundary between the object area and the background area on the line i is detected (when the determination result in Step 142 is 'Yes'), it is determined that the remaining number of boundaries between the object area and the background area on the line i within the range for which charge has not yet been read is 0 or 1.

Therefore, in Step 150, it is determined whether the number of pixels $j_{Bi}$ in the background area on the line i is 0 (that is, all the pixels in the range of the line i for which charge has not yet been read belong to the object area) or jmax−j (that is, all the pixels in the range of the line i for which charge has not been read belong to the background area). If the determination result is 'Yes', it is determined that there is no boundary between the object area and the background area in the range of the line i for which charge has not yet been read (the remaining number of boundaries is 0; corresponding to line E shown in FIG. 8B), and the process proceeds to Step 158.

On the other hand, if the determination result in Step 150 is 'No', it is determined that there is one boundary between the object area and the background area in the range of the line for which charge has not yet been read. Therefore, in Step 152, it is determined whether the unit region (i, j) belongs to the background area of the image. If the determination result is 'Yes', it is determined that $j_{Bi}$ unit regions from the unit region (i, j) all belong to the background area and the unit regions from the next unit region (a (j+$j_{Bi}$+1)-th unit region) to the last unit region in the object area are continuously arranged. Therefore, the process proceeds to Step 154 and a value (j+$j_{Bi}$) is stored in the memory as the position of a boundary that changes from the background area to the object area on the line i. Then, the process proceeds to Step 158. If the determination result in Step 152 is 'No', it is determined that (jmax−j−$j_{Bi}$) unit regions from the unit region (i, j) all belong to the object area and the unit regions from the next unit region (a (jmax−$j_{Bi}$+1)-th unit region) to the last unit region in the background area are continuously arranged (corresponding to the line B shown in FIG. 8A and the line D shown in FIG. 8B). Therefore, the process proceeds to Step 156 and a value (jmax−$j_{Bi}$) is stored in the memory as the position of a boundary that changes from the object area to the background area on the line i. Then, the process proceeds to Step 158.

The estimation results of the positions of all the boundaries on the line i are stored in the memory by the above-mentioned process. Therefore, the estimation completion flag $F_{Fi}$ is set to 1 in Step 158, and the process proceeds to Step 160. As described above, the boundary position on each line having the estimation completion flag $F_{Fi}$ initially set to 0 is estimated when the read current value of a unit region corresponding to the boundary position is acquired. The boundary positions on the lines are estimated at different times. However, for any line having the estimation completion flag $F_{Fi}$ initially set to 0, when the read current value of a unit region corresponding to the boundary position is acquired, the distribution of the object area and the background area within the range of the same line for which charge has not been read is estimated based on the number of pixels $j_{Bi}$ in the background area calculated before an image is read, and the boundary position of the line is estimated. Therefore, the boundary position estimating process is completely performed for all of the lines before an image is completely read from the radiographic image detector 20.

Next, the leakage current correcting process for preview performed in parallel with the image reading process will be described with reference to the flowcharts shown in FIGS. 9A and 9B. In the leakage current correcting process for preview, first, in Step 200, a variable $j_i$ (i=1 to imax) for identifying a unit region of the line i which is to undergo leakage current correction, is set to 1 as an initial value. In Step 202, the variable i is set to 1. In Step 204, it is determined whether the leakage correction flag $F_{Li}$ of the line i is 1. If the determination result is 'No', the process proceeds to Step 208. On the other hand, if the determination result is 'Yes', the variable i is recorded in a predetermined table in Step 206 and the process proceeds to Step 208. In Step 208, it is determined whether the variable i has reached the total number of lines imax. If the determination result is 'No', the variable i is increased by 1 in Step 210 and the process returns to Step 204. Steps 204 to 210 are repeatedly performed until the determination result in Step 208 becomes 'Yes'. In this way, only the variables i corresponding to lines having their leakage correction flag $F_{Li}$ set to 1, that is, lines whose leakage current is to be corrected are recorded in the predetermined table.

If the determination result in Step 208 is 'Yes', the process proceeds to Step 212, and it is determined whether the variable i is recorded in the predetermined table. If the determination result is 'No', then there is no line in the image read from the radiographic image detector 20 that includes the object area and the background area therein, and it is determined that the image is not a normal image, and imaging has failed or it is likely that an error has occurred in the apparatus. Therefore, if the determination result in Step 212 is 'No', a warning is issued. For example, a warning sound is generated or a message is displayed on the display 52, and the process ends.

The error determination is not limited to the determination in Step 212. For example, the error determination may be performed based on whether the number of variables i recorded in the predetermined table is equal to or more than a predetermined value, or it may be performed based on whether the variable i recorded in the predetermined table is continuous (whether the variable is discrete). In addition, an allowable range of a distribution range of the object area of the image upon performing an imaging operation suitable for each type of image may be predetermined (for example, when the object is a breast, a CC view and an MLO view), and it may be determined whether the distribution range of the object area that can be determined from the variable i recorded in a predetermined table is beyond the allowable range. The above-mentioned various kinds of error determining processes may be performed when the determination results in Steps 106 and 114 of the image reading process shown in FIG. 7A (whether the number of pixels $j_{Bi}$ in the background area on each line is 0, or is the total number of pixels jmax (the total number of unit regions), or is between these two values) can be acquired, and the estimation result of the position of the boundary between the object area and the background area may not be required. Therefore, when the leakage current correction is not performed, and only the error determination is performed, the estimation of the position of the boundary between the object area and the background area may be omitted. The above-described exemplary embodiment is also included in the scope of the invention.

On the other hand, if the determination result in Step 212 is 'Yes', the process proceeds to Step 214. From Step 214, a simple leakage current correcting process is performed on the image (data) that is read from the radiographic image detector 20 by the image reading process, thereby generating image data to be displayed as a preview image. That is, first, in Step 214, one variable i is extracted from the predetermined table. In Step 216, it is determined whether the estimation completion flag $F_{Fi}$ of the line i corresponding to the variable i extracted in Step 214 is 1, that is, whether estimation of the position of the boundary between the object area and the background area on the line i has been completed. If the determination result is 'No', the process returns to Step 214, and a process of extracting the variable i one by one from the predetermined table is repeatedly performed until the determination result in Step 216 is 'Yes'.

If the determination result in Step 216 is 'Yes', the process proceeds to Step 218 and the variable $j_i$ of the line i is set to the variable j. In Step 220, it is determined whether the data $I_{ij}$ of the j-th unit region (i, j) on the line i is stored in the memory. If the determination result is 'Yes', the process proceeds to Step 224, and it is determined whether the unit region (i, j) belongs to the background area of the image based on the read current value of the unit region (i, j). If the determination result is 'Yes', Steps 226 to 232 are skipped and the process proceeds to Step 234. In this way, the unit region belonging to the background area of the image in a unit region group corresponding to the line i is excluded from the leakage current correction objects. However, the invention is not limited thereto, and the leakage current correcting process may be performed on the read current value $I_{ij}$ of the unit region belonging to the background area.

On the other hand, if the determination result in Step 224 is 'Yes' (if the unit region (i, j) belongs to the object area of the image), the process proceeds to Step 226. In Steps 226 to 232, simple leakage current correction for a preview image is performed on the read current value of the unit region (i, j). In this exemplary embodiment, the simple leakage current correction for a preview image is performed on the read current value $I_{ij}$ of the unit region (i, j) according to the following Expression 4.

$$I'_{ij} \leftarrow I_{ij} + n \cdot A \exp(-\alpha t) \quad \text{Expression 4}$$

In Expression 4, t indicates the time elapsed from when the application of a high voltage to the radiographic image detector 20 is stopped, to when charge is read from the unit region (i, j); A indicates a coefficient; $\alpha$ indicates a time constant, and n indicates the number of unit regions which correspond to the line i that includes the unit region (i, j) and which belong to the background area of the image and from which charge has not been read during the reading of charge from the unit region (i, j) (the number of unit regions belonging to the background areas among the hatched unit regions shown in FIG. 6). In this exemplary embodiment, since the leakage current superimposed with the read current flows in a direction opposite to the flow direction of the read current (the read current during the reading of charge decreases to the extent of the leakage current), an equation obtained by adding the second term of the right side of Expression 4 to the first term of the right side may be used as an expression for estimating a leakage current. However, if the leakage current and the read current flow in the same direction, an equation obtained by subtracting the second term of the right side of Expression 4 from the first term of the right side of Expression 4 may be used as an expression for estimating a leakage current.

As can be clearly seen from the comparison between the estimation of the leakage current when the radiation dose is large and the estimation of the leakage current when the radiation dose is small, shown in FIG. 5B, the amount of leakage current from each unit region of the radiographic image detector 20 depends on the radiation dose emitted to each unit region, that is, the amount of charge in each unit region. Therefore, when accurately applying leakage current correction to a diagnosis image, all the unit regions which correspond to the line i that includes the unit region (i, j) and from which charge has not been read during the reading of charge from the unit region (i, j) are considered as objects whose leakage current is to be considered, and the leakage current is corrected using, as the coefficient A, a value (that is set such that the coefficient A increases as the amount of charge increases) that corresponds to the amount of charge (read current value) read from each unit region whose leakage current is to be considered.

However, the leakage current correcting process for preview according to this exemplary embodiment is performed in parallel with the image reading process shown in FIGS. 7A and 7B. Therefore, when the leakage current correcting process is performed on the read current value of the unit region (i, j), it is possible that charge is not completely read from all the unit regions which correspond to the line i that includes the unit region (i, j) and from which charge has not been read during the reading of charge from the unit region (i, j). Further, it is desirable that the preview image be displayed as quickly as possible. Therefore, in the leakage current correcting process for preview according to this exemplary embodiment, the unit regions whose current leakage is to be considered are limited to the unit regions which correspond to the line i that includes the unit region (i, j) and which belong to the background area of the image and from which charge has not been read during the reading of charge from the unit region (i, j) (hereinafter, these unit regions are also referred to as "unit regions whose leakage current is to be considered in simple leakage current correction"). In addition, it is assumed that the radiation dose (the amount of charge held) emitted to each unit region belonging to the background area of the image is uniform (a value corresponding to the radiation dose X during imaging), and the leakage current correcting process is performed using the value corresponding to the radiation dose X as the coefficient A.

That is, first, in Step 226, the number of unit regions n whose leakage current is to be considered in the simple leakage current correction performed on the unit region (i, j) is calculated based on the position of the boundary between the object area and the background area on the line i estimated by the image reading process (see FIGS. 7A and 7B). In this exemplary embodiment, the time constant $\alpha$ and the coefficient A corresponding to the radiation dose X are stored as a portion of leakage current correction data in the storage unit 50A in advance. In Step 228, the radiation dose X during imaging is acquired, and the coefficient A corresponding to the acquired radiation dose X during imaging and the constant $\alpha$ are acquired from the storage unit 50A. In Step 230, the time t elapsed from when the application of a high voltage to the radiographic image detector 20 is stopped to when charge from the unit region (i, j) is acquired based on the variable j of the unit region (i, j) is read.

In general, a time t1 elapsed from when the application of a high voltage to the radiographic image detector 20 is stopped to when reading of an image (charge) from the radiographic image detector 20 is started, and a time t2 required to read the charge in the unit regions corresponding to one line in the scanning direction from the radiographic image detector 20 are constant. Therefore, for example, the elapsed time t may be acquired by recording the times t1 and t2 as leakage current correction data, reading the times t1 and t2 from the storage unit 50A in Step 230, and adding the product of the variable j of the unit region (i, j) and the time t2 to the time t1. As the elapsed time t in Expression 4, the time elapsed from when the reading of charge from the radiographic image detector 20 is started to when charge from the unit region (i, j) (the time corresponding to the product of the variable j of the unit region (i, j) and the time t2) is read may be used, instead of the time elapsed from when the application of a high voltage to the radiographic image detector 20 is stopped to when charge from the unit region (i, j) is read.

In Step 232, Expression 4 included in the leakage current correction data is read from the storage unit 50A, and the read current value of the unit region (i, j), the coefficient A and the time constant α acquired in Step 228, and the elapsed time t acquired in Step 230 are substituted into the read Expression 4 to calculate a new read current value $I'_{ij}$. The calculation result is stored in the memory. In this way, the read current value $I'_{ij}$ of the unit region (i, j) is corrected according to the leakage currents from n unit regions whose leakage currents are considered, which are superimposed with the read current during the reading of current from the unit region (i, j), and the influence of the leakage currents from the n unit regions whose leakage currents are considered is removed from the read current value $I'_{ij}$ of the unit region (i, j).

In the leakage current correcting process, among the unit regions which correspond to the line i that includes the unit region (i, j) and from which charge has not been read during the reading of charge from the unit region (i, j), the unit regions belonging to the object area of the image are excluded from the unit regions whose leakage current is considered, but the invention is not limited thereto. For example, the leakage currents from all of the unit regions which correspond to the line i including the unit region (i, j) and from which charge has not been read during the reading of charge from the unit region (i, j) may be considered. In this case, the leakage current from the unit region belonging to the object area may be calculated based on the second term on the right side of Expression 4 using as the coefficient A in Expression 4 a value corresponding to the unit region belonging to the object area (the value may be constant, or it may vary with a gradient that is smaller than that of the coefficient A for the unit region belonging to the background area when the radiation dose X varies). Since a very small amount of leakage current flows from each unit region belonging to the object area, a predetermined fixed value may be used as the leakage current from each unit region belonging to the object area.

Since the time t2 required to read the charge in the unit regions corresponding to one line in the main scanning direction from the radiographic image detector 20 is constant, a leakage current estimation expression composed of an exponential function having as a variable the position of the unit region (i, j) in the movement direction of the line light source 54 (sub-scanning direction) (the position may be the variable j of the unit region (i, j) or the distance from the movement start position of the line light source 54 that can be calculated from the variable j to the position of a target unit region in the sub-scanning direction) may be used instead of the leakage current estimation expression in the second term on the right side of Expression 4. In this case, it is also possible to estimate a leakage current with the same accuracy as that when the leakage current estimation expression in the second term on the right side of Expression 4 is used.

In Step 234, it is determined whether the variable j has reached the total number of pixels jmax (the total number of unit regions) on one line. If the determination result is 'No', the variable j is increased by 1 in Step 236 and the process returns to Step 220. Then, Steps 220 to 236 are repeatedly performed until the determination result in Step 234 is 'Yes'.

In this way, a simple leakage current correcting process for the read current value of the unit region (i, j) is sequentially performed on the unit regions belonging to the object area among the unit regions on the line i. Since the leakage current correcting process for preview according to this exemplary embodiment is performed in parallel with the image reading process, the progress of the leakage current correcting process follows the progress of the reading of an image from the radiographic image detector 20. Therefore, when the read current value of a unit region (i, j) whose leakage current is to be corrected is to be read from the memory, a state may occur in which charge has not yet been read from the unit region (i, j) and the read current value $I_{ij}$ is not stored in the memory.

In this case, the determination result in Step 220 is 'No' and the process proceeds to Step 222 to set the variable $j_i$ of the line i to j, then the process returns to Step 214. In this way, the leakage current correction of the line i is interrupted, and the leakage current correcting process is performed on other lines for which leakage current correction has not been completed. When the variable i of the line i is read from the predetermined table again in Step 214, the variable j is set to the variable $j_i$ of the line i in Step 218, and the leakage current correction of the line i is resumed using, as an initial correction object, a unit region whose read current value $I_{ij}$ was not stored in the memory in the previous leakage current correction of the line i.

When Steps 220 to 236 are performed on the last unit region (the unit region having the variable j=jmax) of a line having a leakage correction flag $F_{Li}$ initially set to 1, and for which leakage current correction is completed, the determination result in Step 234 is 'Yes' and the process proceeds to Step 238. Then, the leakage correction flag $F_{Li}$ of the line i whose leakage current has been completely corrected is then set to 0, which indicates that correction has been completed. In Step 240, the variable i corresponding to the line i whose leakage current has been completely corrected is removed from the predetermined table. Then, in Step 242, it is determined whether the variable i is recorded in the predetermined table. If the determination result is 'No', the process returns to Step 214, and the leakage current correcting process is performed on other lines whose leakage currents have not been corrected yet. As described above, the variable i of the line whose leakage current has not been completely corrected is removed from the predetermined table. Therefore, when the leakage current correcting process is completely performed for each of the lines having a leakage correction flag $F_{Li}$ initially set to 1, the determination result in Step 242 is 'No' and the leakage current correcting process for preview ends.

As described above, since the leakage current correcting process for preview according to this exemplary embodiment is performed in parallel with the image reading process, it is possible to complete the process in a relative short period of time from the completion of the reading of an image from the radiographic image detector 20. An image indicated by the image data obtained by the leakage current correcting process for preview is instantaneously displayed as a preview image on the display 52. Therefore, even when the leakage current correction of a preview image is omitted, it is possible to present a high-resolution preview image to the operator such that the operator can determine whether the imaging range or the captured image is appropriate based on the preview image as quickly as possible (while the operator performs the determination, high-accuracy leakage current correction can be performed on the image read from the radiographic image detector 20 to obtain a diagnosis image). In addition, if it is determined that the imaging range or the captured image is not appropriate, it is possible to rapidly image again.

The invention is not limited to the above-mentioned structure in which the image data obtained by the leakage current correcting process for preview is displayed as a preview image on the display 52. For example, the image data may be stored in a flash memory or other information recording media, or it may be recorded as an image on a sheet-shaped recording medium by a recording apparatus such as a printer.

In the image reading process (FIGS. 7A and 7B) according to this exemplary embodiment or in the stage in which one boundary between the object area and the background area on the line is detected, it is determined whether the remaining number of boundaries between the object area and the background area on the same line is 0 or 1, and when the remaining number of boundaries is 1, the position of the one boundary is estimated. However, the invention is not limited thereto. For example, in the CC view, which is one kind of object image, for example breast image, as can be clearly seen from FIG. 8A, the number of boundaries between the object area and the background areas on the line including the object area and the background area is 2, and the object areas of the image are distributed so as to be symmetric with respect to an axis that passes through the center of the image in the sub-scanning direction and is parallel with the main scanning direction. Therefore, when the image that is imaged and is held as charge in the radiographic image detector 20 is the CC view or an image similar to the CC view, it may be assumed that two background areas with the same length on the line including the object areas and the background areas are arranged at both ends of the line in the sub-scanning direction, and the position of the boundary between the object area and the background area may be estimated based on the number $j_{Bi}$ of pixels in the background area and the total number jmax of pixels (the total number of unit regions) of one line. In this case, the estimation accuracy of the boundary position is reduced, but it is possible to estimate the boundary position before an image is read from the radiographic image detector 20 (in the stage in which the number $j_{Bi}$ of pixels in the background area is calculated). Therefore, it is possible to rapidly complete the correction of the leakage current and display a preview image. In addition, it is possible to reduce the load of the control device 50 (image processing unit 70). In this exemplary embodiment, the assumed value of the ratio is 50% (1:1). However, the assumed value of the ratio may vary depending on, for example, the kind of image held as charge in the radiographic image detector 20 after imaging is performed.

In the above-described exemplary embodiment, the image of the breast, which is an object, is read from the radiographic image detector 20, the position of the boundary between the object area and the background area is estimated, and simple leakage current correction is performed. However, the invention is not limited thereto. For example, parts of the human body other than the breast or materials other than the human body may be used as the object. When the object is a part of the human body other than the breast, the number of boundaries between the object area and the background area on the line including the object areas and the background areas or the upper limit thereof is not limited to '2', unlike when the object is the breast. For example, when the upper limit of the number of boundaries between the object area and the background area is 3 or more, it is determined whether the number $j_B$, of pixels in the background area is 0 or equal to the remaining number of pixels (jmax−j) (determination corresponding to Step 150 in FIG. 7B) whenever one boundary between the object area and the background area on the line is detected. If the determination result is 'Yes', it is determined that the remaining number of boundaries is 0 and the process ends. On the other hand, if the determination result is 'No' and the detected number of boundaries is equal to or smaller than the upper limit minus 2, the boundary between the object area and the background area on the same line is continuously searched. If the detected number of boundaries is equal to or smaller than the upper limit minus 1, Steps 152 to 156 shown in FIG. 7B are performed to detect or estimate the positions of all the boundaries on the line. The above process is performed when the upper limit of the number of boundaries is known. However, when the number of boundaries is known, determination corresponding to Step 150 shown in FIG. 7B is not needed. Therefore, the algorithm is simplified. As such, according to this exemplary embodiment of the invention, when the number of boundaries on the line or the upper limit thereof is known, it is possible to detect or estimate the positions of the boundaries on the line.

In the above-described exemplary embodiment, the estimation result of the ratio between the object area and the background area on the line i or the lengths thereof are stored as the number $j_{Bi}$ of pixels in the background area (a value obtained by converting the length of the background area on the line i into the number of pixels (the number of unit regions)) and is used to estimate the position of the boundary on the line i. However, the invention is not limited thereto. For example, the length of the object area or a value obtained by converting the length into the number of pixels (the number of unit regions) may be used, or the ratio between the object area and the background area on the line (for example, the ratio ($I_{L2i}/I_{L1i}$) between the first leakage current value $I_{L1i}$ and the second leakage current value $I_{L2i}$) may be used, instead of the number $j_{Bi}$ of pixels in the background area.

In the above-described exemplary embodiment, the estimation result of the position of the boundary between the object area and the background area on the line is used in the leakage current correcting process, but the invention is not limited thereto. For example, image processing, such as a process of generating a boundary indication image indicating the position of the boundary between the object area and the background area in the image (for example, an image in which the object area and the background area are displayed in different colors, or an image in which the boundary between the object area and the background area is highlighted), may be performed based on the estimation result of the position of the boundary between the object area and the background area on the line. In addition, the process of generating the boundary indication image is simpler than the leakage current correcting process for preview shown in FIGS. 9A and 9B. Therefore, when the generated boundary indication image is displayed on the display 52 before a preview image is displayed, it is possible to determine whether the imaging range is appropriate as quickly as possible. The density of the pixel (unit region) whose value is determined by the leakage current correcting process for preview may be changed to a value defining the density of the boundary indication image, and the boundary indication image displayed on the display 52 may be gradually changed to a preview image.

Figure 10:
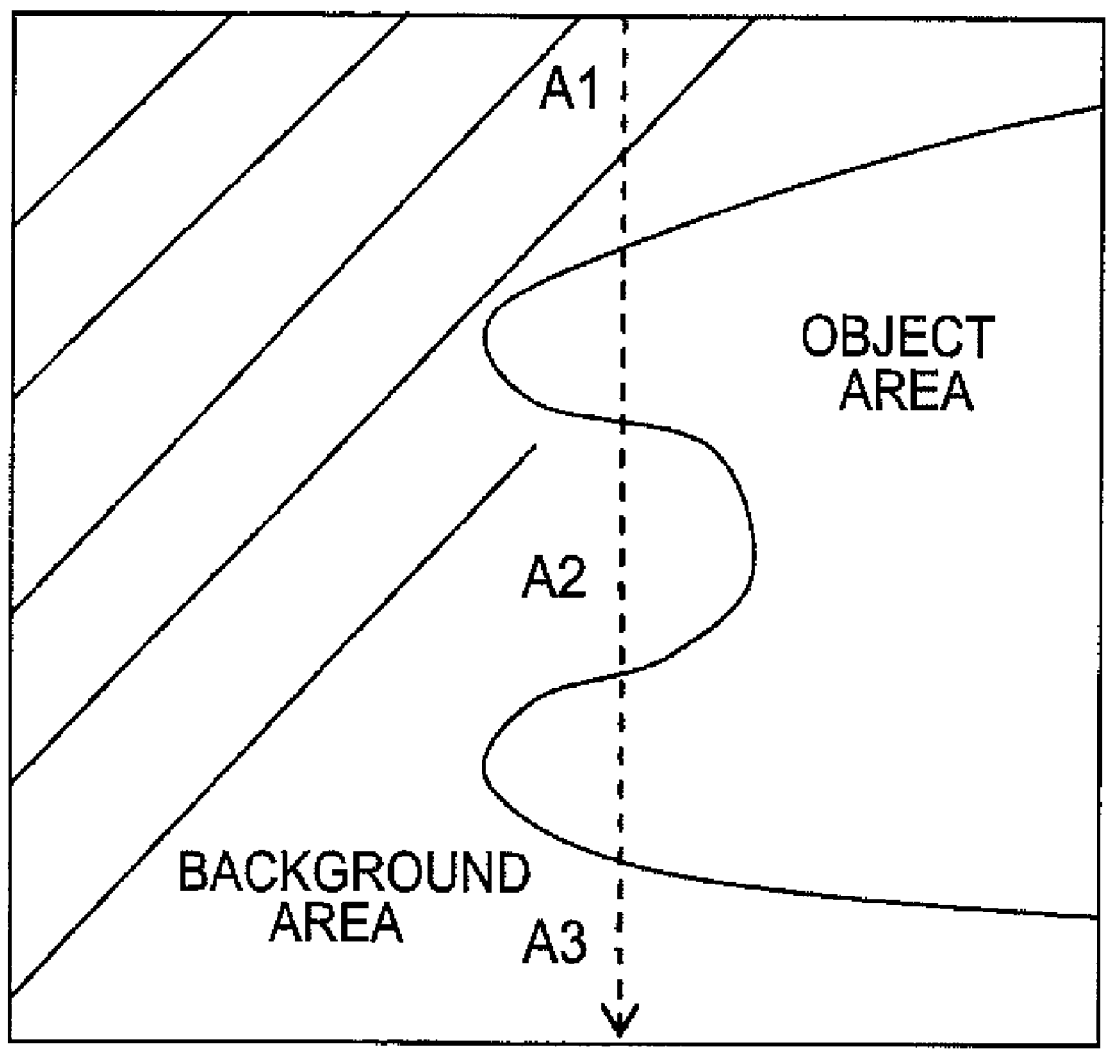
FIG. 10 is a diagram illustrating an image for describing leakage current correction that does not use the estimation result of the position of the boundary between the object area and the background area.

In the above-described exemplary embodiment, the estimation result of the position of the boundary between the object area and the background area on the line is used to perform the leakage current correcting process, but the invention is not limited thereto. The estimation result of the ratio between the object area and the background area on the line or the lengths thereof may be used to perform the leakage current correcting process. For example, when the object area and the background area in the image that is imaged and held as charge in the radiographic image detector 20 are distributed as shown in FIG. 10, the number $j_{Bi}$ of pixels in the background area, which is an example of the estimation result of the ratio between the object area and the background area on the line or the lengths thereof, indicates the total length of the background area on the line (for example, the number $j_B$, of pixels in the background area on the line represented by a dashed line in FIG. 10 indicates the sum of the lengths of background areas A1, A2, and A3 on the line). Therefore, it is possible to know that the background area is divided into the background areas A1, A2, and A3 or the number of boundaries between the object area and the background area on the line is 4 from the number $j_{Bi}$ of pixels in the background area.

However, as can be clearly seen from Expression 4, the simple leakage current correction process can be performed when the number n of unit regions whose leakage currents will be considered (the unit regions which correspond to the line including the unit region (i, j) to be corrected and belong to the background area of the image, and from which charge has not been read during the reading of charge from the unit region (i, j)) is known. Therefore, for example, the number $j_{Bi}$ of pixels in the background area on each line that is calculated as quickly as possible by the image reading process (FIGS. 7A and 7B) is stored as a different variable (here, for convenience, referred to as the 'remaining length of the background area'). In the leakage current correcting process for preview shown in FIGS. 9A and 9B, when the read current value $I_{ij}$ of each unit region corresponding to the line i is sequentially read and leakage current correction is performed, the 'remaining length of the background area' of the line i is decreased by 1 whenever it is determined that the unit region to be corrected belongs to the background area of the image based on the read current value $I_{ij}$. In this case, it is possible to use the 'remaining length of the background area' as 'n' of Expression 4. Therefore, it is possible to correct the leakage current without using the estimation result of the position of the boundary between the object area and the background area on the line.

In the above-described exemplary embodiment of the invention, the light-reading-type radiographic image detector 20 is given as an example of the radiographic image detector, but the invention is not limited thereto. For example, the invention may be applied to other types of radiographic image detectors such as a TFT-type radiographic image detector. In this case, since an electric resistance for holding the charge in each unit region is not infinity, a leakage current occurs in each unit region of the radiographic image detector, and the amount of leakage current gradually varies over time. Therefore, when the leakage current correction according to the invention is applied, it is possible to accurately correct the influence of the leakage current.

In the above-described exemplary embodiment of the invention, the image processing program is stored (installed) in the storage unit 50A of the control device 50 in advance. However, the image processing program according to the invention may be provided with being recorded on a recording medium, such as a CD-ROM or a DVD-ROM.

INDUSTRIAL APPLICABILITY

The invention can be mainly applied to correct a radiographic imaged by a radiography apparatus for medical diagnosis. According to the invention, it is possible to perform image processing with high correction accuracy.

The invention claimed is:

1. An image processing apparatus comprising:
a storage unit that stores a first leakage current value which is output through a signal line provided in a predetermined direction in a radiographic image detector which converts emitted radiation into a charge and stores and holds the charge, a charge corresponding to uniformly emitted radiation being held in the radiographic image detector; and
an estimating unit that estimates a ratio between an object area and a background area on a line arranged along the signal line in an image which is held as the charge in the radiographic image detector, or estimates lengths of the object area and the background area, based on the ratio between the first leakage current value stored in the storage unit, and a second leakage current value output through the signal line when radiation passing through an object is emitted to the radiographic image detector, a charge corresponding to the radiation passing through the object being held in the radiographic image detector.

2. The image processing apparatus of claim 1, wherein when the number of boundaries between the object area and the background area on the line arranged along the signal line, or the upper limit of the number of boundaries, is known, the estimating unit estimates the ratio between the object area and the background area on the line arranged along the signal line, or estimates lengths of the object area and the background area, and estimates the position of a boundary between the object area and the background area on the line arranged along the signal line based on the estimated ratio or the estimated lengths and the known number of boundaries.

3. The image processing apparatus of claim 2, wherein the estimating unit detects the position of the boundary between the object area and the background area in the range of the line arranged along the signal line in which the charge is read as a current, based on a variation in the current when the charge is sequentially read as the current from each unit region read through the signal line, and estimates the position of the boundary between the object area and the background area in the range of the line arranged along the signal line for which charge has not been read, based on the detected position of the boundary and the estimated ratio between the object area and the background area or the estimated lengths of the object area and the background area.

4. The image processing apparatus of claim 2, wherein the estimating unit estimates the position of the boundary between the object area and the background area on the line arranged along the signal line, based on a predetermined assumed value of the ratio between a plurality of background areas on the line arranged along the signal line, and the estimated ratio between the object area and the background area or the estimated lengths of the object area and the background area.

5. The image processing apparatus of claim 1, wherein
the storage unit stores the first leakage current values when a plurality of different radiation doses is uniformly emitted to the radiographic image detector, and
the estimating unit performs the estimation based on the first leakage current value corresponding to the radiation dose emitted to the object of the first leakage current values stored in the storage unit.

6. The image processing apparatus of claim 1, wherein
the radiographic image detector includes a plurality of signal lines,
the storage unit stores the first leakage current value of each of the signal lines, and
the estimating unit performs estimation for each of the signal lines based on the corresponding first leakage current value of the first leakage current values stored for each signal line in the storage unit.

7. The image processing apparatus of claim 2, further comprising:
a leakage current correcting unit that performs a leakage current correcting process, the process including estimating a leakage current superimposed with a read current when charge is read from each unit region belonging to at least the object area of read unit regions corresponding to the signal line, based on the ratio between the object area and the background area on the line arranged along the signal line, or the lengths of the object area and the background area, or the position of the boundary between the object area and the background area, which are estimated by the estimating unit, and the process including correcting corresponding data based on the estimation result of the leakage current.

8. The image processing apparatus of claim 7, wherein the leakage current correcting unit
calculates the number of unit regions belonging to the object area and the number of unit regions belonging to the background area, of the unit regions which are disposed in the predetermined direction on the same signal line as the unit region that is the object of correction, and from which charge was not read during the reading of charge from the unit region that is the object of correction, based on the ratio between the object area and the background area on the line arranged along the signal line, or the lengths of the object area and the background area, or the position of the boundary between the object area and the background area, which are estimated by the estimating unit;
excludes the unit regions belonging to the object area from a leakage current estimation object, and
estimates only the leakage current of the unit regions belonging to the background area, thereby estimating the leakage current superimposed with the read current when the charge of the unit region that is the object of correction is read.

9. The image processing apparatus of claim 7, further comprising:
an image processing unit that performs image processing to generate a boundary indication image indicating the position of the boundary between the object area and the background area based on the position of the boundary between the object area and the background area on the line arranged along the signal line which is estimated by the estimating unit.

10. The image processing apparatus of claim 9, wherein the leakage current correcting unit or the image processing unit performs the leakage current correction or the image processing in parallel with a process of sequentially reading the charge from each unit region read through the signal line as a current.

11. The image processing apparatus of claim 10, further comprising a display control unit that controls a display unit to display an image obtained by the leakage current correction by the leakage current correcting unit, or an image obtained by the image processing by the image processing unit.

12. The image processing apparatus of claim 1, wherein the radiographic image detector includes a plurality of read electrodes arranged in a direction intersecting the predetermined direction as the signal lines,
when a light is emitted, a charge corresponding to the amount of charge held in a unit region corresponding to a point to which the light is emitted is output as a current through a corresponding read electrode, and
the charge held in the radiographic image detector is read by scanning, in the predetermined direction, the point of the radiographic image detector to which light is emitted.

13. The image processing apparatus of claim 1, wherein the object is a breast.

14. An image processing method comprising:
storing, in a storage unit, a first leakage current value which is output through a signal line provided in a predetermined direction in a radiographic image detector, which converts emitted radiation into a charge and stores and holds the charge, a charge corresponding to uniformly emitted radiation being held in the radiographic image detector; and
estimating a ratio between an object area and a background area on a line arranged along the signal line in an image which is held as the charge in the radiographic image detector, or estimating the lengths of the object area and the background area, based on the ratio between the first leakage current value stored in the storage unit, and a second leakage current value output through the signal line when radiation passing through an object is emitted to the radiographic image detector, a charge corresponding to the radiation passing through the object being held in the radiographic image detector.

15. The image processing method of claim 14, wherein estimating the ratio or the length includes:
when the number of boundaries between the object area and the background area on the line arranged along the signal line or the upper limit of the number of boundaries is known,
estimating the ratio between the object area and the background area on the line arranged along the signal line, or estimates the lengths of the object area and the background area; and
estimating the position of a boundary between the object area and the background area on the line arranged along the signal line based on the estimated ratio or the estimated lengths and the known number of boundaries.

16. The image processing method of claim 15, wherein estimating the ratio or the length includes:
detecting the position of the boundary between the object area and the background area in the range of the line arranged along the signal line for which charge has not been read as a current, based on a variation in the current when the charge is sequentially read as the current from each unit region read through the signal line; and
estimating the position of the boundary between the object area and the background area in the range of the line arranged along the signal line for which charge has not been read, based on the detected position of the boundary and the estimated ratio between the object area and the background area or the estimated lengths of the object area and the background area.

17. The image processing method of claim 15, wherein estimating the ratio or the length includes:
estimating the position of the boundary between the object area and the background area on the line arranged along the signal line, based on a predetermined assumed value of the ratio between a plurality of background areas on the line arranged along the signal line, and the estimated ratio between the object area and the background area or the estimated lengths of the object area and the background area.

18. An information storage medium storing an image processing program executable by a computer, which is connected to a storage unit storing a first leakage current value output through a signal line provided in a predetermined direction in a radiographic image detector that converts emitted radiation into a charge and stores and holds the charge, the charge corresponding to uniformly emitted radiation being held in the radiographic image detector, wherein the image processing program is executable by the computer to function as:

an estimating unit that estimates a ratio between an object area and a background area on a line arranged along the signal line in an image which is held as the charge in the radiographic image detector, or estimates lengths of the object area and the background area, based on the ratio between the first leakage current value stored in the storage unit, and a second leakage current value output through the signal line when radiation passing through an object is emitted to the radiographic image detector, a charge corresponding to the radiation passing through the object being held in the radiographic image detector.

* * * * *